US008017159B2

(12) United States Patent
Murthy

(10) Patent No.: US 8,017,159 B2
(45) Date of Patent: *Sep. 13, 2011

(54) PHOSPHOLIPID GEL COMPOSITIONS FOR DELIVERY OF APTAMERS AND METHODS OF TREATING CONDITIONS USING SAME

(75) Inventor: Yerramilli V. S. N. Murthy, Apex, NC (US)

(73) Assignee: IDEXX Laboratories, Inc., Westbrook, ME (US)

( * ) Notice: Subject to any disclaimer, the term of this patent is extended or adjusted under 35 U.S.C. 154(b) by 1540 days.

This patent is subject to a terminal disclaimer.

(21) Appl. No.: 11/400,231

(22) Filed: Apr. 10, 2006

(65) Prior Publication Data

US 2007/0110775 A1    May 17, 2007

Related U.S. Application Data

(60) Provisional application No. 60/736,863, filed on Nov. 16, 2005.

(51) Int. Cl.
*A61K 33/34* (2006.01)
*A61K 31/4172* (2006.01)
*A61K 33/26* (2006.01)
*A61K 33/32* (2006.01)
*A61K 31/685* (2006.01)
*A61K 31/405* (2006.01)
*A61K 31/22* (2006.01)
*A61K 31/16* (2006.01)
*A61K 31/40* (2006.01)

(52) U.S. Cl. ........ 424/638; 424/641; 424/646; 424/682; 514/626; 514/78; 514/400; 514/419; 514/550

(58) Field of Classification Search ........................ None
See application file for complete search history.

(56) References Cited

U.S. PATENT DOCUMENTS

| 4,277,497 | A | 7/1981 | Fromantin |
| 5,110,809 | A | 5/1992 | Wang et al. |
| 5,270,163 | A | 12/1993 | Gold et al. |
| 5,475,096 | A | 12/1995 | Gold et al. |
| 6,214,339 | B1 | 4/2001 | Pellico |
| 6,610,841 | B1 | 8/2003 | Warren |
| 6,841,539 | B1 | 1/2005 | Mehta et al. |
| 7,846,472 | B2 * | 12/2010 | Murthy ............ 424/450 |
| 7,854,943 | B2 * | 12/2010 | Murthy ............ 424/450 |
| 7,858,115 | B2 * | 12/2010 | Murthy ............ 424/450 |
| 2001/0003580 | A1 | 6/2001 | Hui et al. |
| 2004/0197408 | A1 | 10/2004 | Gravett |
| 2004/0220264 | A1 | 11/2004 | Yu et al. |
| 2005/0175708 | A1 | 8/2005 | Carrasquillo et al. |

FOREIGN PATENT DOCUMENTS

WO    WO 00/09117    2/2000

OTHER PUBLICATIONS

Griffin, et al., *The Discovery and Characterization of a Novel Nucleotide-Based Thrombin*, Gene 137 (1993), pp. 25-31.

Jenison, et al., *Oligonucleotide Inhibitors of P-Selection-Dependent Neutrophil-Platelet Adhesion*, Antisense & Nucleic Acid Drug Development, vol. 8, (4): 265-279 (1998).
Bell, et al., *Oligonucleotide NX1838 Inhibits VEGF $_{165}$-Mediated Cellular Responses In Vitro*, In Vitro Cellular & Developmental Biology, Journal of the Society for In Vitro Biology, vol. 35 (9), pp. 533-542 (1999).
Watson, et al., *Anti-L-Selectin Aptamers: Binding Characteristics, Pharmacokinetic Parameters, and Activity Against an Intravascular Target In Vivo*, Antisense & Nucleic Acid Drug Development, 10:63-75 (2000), p. 63.
Daniels, et al., *Generation of RNA Aptamers to the G-Protein-Coupled Receptor for Neurotensin, NTS-1*, Analytical Biochemistry 305, pp. 214-226 (2002).
Chen, et al., *Inhibition of Heregulin Signaling by an Aptamer that Preferably Binds to the Oligomeric Form of Human Epidermal Growth Factor Receptor-3*, Proc. Natl. Acad. Sci. U.S.A. 100(16), pp. 9226-9231, PNAS, Aug. 5, 2003.
Khati, et al., Neutralization of Infectivity of Diverse R5 Clinical Isolates of Human Immunodeficiency Virus Type 1 by gp120-Binding 2'F-RNA Aptamers, Journal of Virology, Dec. 2003, pp. 12692-12698.
Vaish, et al., *A Novel, Modification-Dependent ATP-Binding Aptamer Selected from an RNA Library Incorporating a Cationic Functionality*, Biochemistry, 2003, 42, pp. 8842-8851.
Ellington, et al., *In Vitro Selection of RNA Molecules that Bind Specific Ligands*, Nature, vol. 346, Aug. 30, 1990, pp. 818-822.
Turek, et al., *Systematic Evolution of Ligands by Exponential Enrirchment: RNA Ligands to Bacteriophage T4 DNA Polymerase*, Aug. 3, 1990, Science, vol. 249, pp. 505-510.
Wlotzka, et al., In Vivo Properties of an Anti GnRH Spiegelmer: An example of an Oligonucleotide-Based Therapeutic Substance Class, (2002), Proc. Natl. Acad. Sci. U.S.A. 99 (13): pp. 8898-8902.
Reyderman, et al. (1998), *Pharmacokinetics and Biodistribution of a Nucleotide-Based Thrombin Inhibitor in Rats*, Pharmaceutical Research, vol. 15, No. 6, 1998, pp. 904-910.
Tucker, et al., *Detection and Plasma Pharmacokinetics of an Anti-Vascular Endothelian Growth Factor Oligonucleotide-Aptamer (NX1838) in Rhesus Monkeys*, Journal of Chromatography B, 732 (1999), pp. 203-212. Green, et al., Nuclease-Resistant Nucleic Acid Ligands to Vascular Permeability Factor/Vascular Endothlial Growth Factor, Chem. & Biol. 2(10), pp. 683-695, 1995.
Jellinek, et al., *Potent 2'-Amino-2'-Deoxypyrimidine RNA Inhibitors of Basic Fibroblast Growth Factor*, Biochemistry 1995, 34, pp. 11363-11372.
Ruckman, et al., *2'-Fluoropyrimidine RNA-Based Aptamers to the 165-Amino. Acid Form of Vascular Endothelial Growth Factor ($VEGH_{165}$)*, The Journal of Biological Chemistry, vol. 273, No. 32, Issue of Aug. 7, 1998, pp. 20556-20567.
Uhlmann, et al., *Use of Minimally Modified Antisense Oligonucleotides for Specific Inhibition of Gene Expression*, in Methods in Enzymology, Antisense Technology, Part A, General Methods, Methods of Delivery, and RNA Studies, vol. 313, edited by M. Ian Phillips, Academic Press, San Diego., pp. 268-284, (2000).
Burmeister, et al., *Direct in Vitro Selection of a 2'-O-Methyl Aptamer to VEGF*, Chemistry and Biology, vol. 12, pp. 25-33, Jan. 2005.

* cited by examiner

*Primary Examiner* — Shanon A Foley
(74) *Attorney, Agent, or Firm* — Haynes and Boone, LLP

(57) ABSTRACT

The present invention relates to pharmaceutical compositions in the form of a gel for controlled- or sustained-release of an aptamer and to methods for treating or preventing a condition in an animal by administering to an animal in need thereof the pharmaceutical compositions.

70 Claims, No Drawings

PHOSPHOLIPID GEL COMPOSITIONS FOR DELIVERY OF APTAMERS AND METHODS OF TREATING CONDITIONS USING SAME

1. CROSS-REFERENCE TO RELATED APPLICATIONS

This application claims the benefit of U.S. provisional application No. 60/736,863, filed Nov. 16, 2005, the contents of which are incorporated herein by reference thereto.

2. STATEMENT REGARDING FEDERALLY SPONSORED RESEARCH OR DEVELOPMENT

Not Applicable.

3. INCORPORATION-BY-REFERENCE OF MATERIAL SUBMITTED ON A COMPACT DISC

Not Applicable.

4. BACKGROUND OF THE INVENTION 4.1 Field of the Invention

The present invention relates to pharmaceutical compositions in the form of a gel for controlled- or sustained-release of an aptamer and to methods for treating or preventing a condition in an animal by administering to an animal in need thereof the pharmaceutical compositions. The pharmaceutical compositions are suitable for oral, topical, otic, injectable, and ophthalmic administration.

4.2 Description of Related Art

It is often desirable to administer drugs using controlled- or sustained-release formulations that can maintain at least a minimum therapeutic level, for example, a blood level, of the drug over extended periods of time. These controlled- or sustained-release formulations reduce the frequency of dosing, for enhanced convenience and compliance, and also reduce the severity and frequency of side effects. For example, by maintaining substantially constant blood levels and avoiding blood level fluctuations of the drug, such as are associated with conventional immediate release formulations that are administered several times a day, controlled- or sustained-release formulations can provide a better therapeutic profile than is obtainable with conventional immediate release formulations.

Known methods for controlled- or sustained-drug release include implanted devices, such as osmotic pumps, and drug dispersed in a biocompatible polymer matrix, which can be implanted, administered orally, or injected. Examples of biocompatible polymers used in such applications include poly (lactic acid) and poly(lactic acid-co-glycolic acid). The polymer typically undergoes slow hydrolysis in vivo to continually release the entrapped drug over time. The polymer degradation products are non-toxic and absorbed or metabolized by the body. For example, when the biocompatible polymer is poly(lactic acid) or poly(lactic acid-co-glycolic acid), the degradation products are the parent acids, lactic acid and glycolic acid, which are absorbed by the body.

U.S. Pat. No. 5,110,809 to Wang et al. discloses a stable anhydrous gel formulations for topical antifungal use containing an imidazole, a steroid, a co-solvent system comprising monohydric and dihydric alcohols, and a hydroxyalkylcellulose gellant.

International Publication No. WO 00/09117 discloses topical pharmaceutical compositions containing nimesulfide, a non-steroidal anti-inflammatory agent having poor solubility in water.

U.S. Pat. No. 6,214,339 to Pellico discloses a treatment for otitis externa in cats and dogs that comprises administering a substantially non-aqueous, di-enzymatic therapeutic composition, in a liquid or gel fluid carrier. An illustrative composition contains glucose, glucose oxidase, potassium iodide, and lactoperoxidase in a fluid mixture of glycerol and propylene glycol.

Eurasian Patent No. EA 0002978 B1 claims in the primary independent claim a process for preparing a phospholipid suspension.

U.S. patent application no. US 2004/0220264 discloses compositions, methods of making the compositions, and uses of compositions that include a molecular complex between an acidic pharmaceutical drug and a functional substance. The functional substance can be an alkaline amino acid, an amino acid amide, an amino acid ester, or a related amino acid. The compositions are allegedly useful for delivering the drug into cutaneous tissue.

U.S. patent application no. US 2004/0197408 discloses formulations of a diblock copolymer having a hydrophobic block and hydrophilic block, an additive selected from an amino acid, and an oligopeptide. The formulations, when admixed with water, form drug delivery vehicles in micellar form.

Aptamers, are oligonucleotides, which can be synthetic or natural, that bind to a particular target molecule, such as a protein or metabolite. Typically, the binding is through interactions other than classic Watson-Crick base pairing.

Aptamers represent a promising class of therapeutic agents currently in pre-clinical and clinical development. Like biologics, e.g., peptides or monoclonal antibodies, aptamers are capable of binding specifically to molecular targets and, through binding, inhibiting target function. A typical aptamer is 10-15 kDa in size (i.e., 30-45 nucleotides), binds its target with sub-nanomolar affinity, and discriminates among closely related targets (e.g., will typically not bind other proteins from the same gene family) (Griffin, et al. (1993), *Gene* 137(1): 25-31; Jenison, et al. (1998), *Antisense Nucleic Acid Drug Dev.* 8(4): 265-79; Bell, et al. (1999), *In Vitro Cell. Dev. Biol. Anim.* 35(9): 533-42; Watson, et al. (2000), *Antisense Nucleic Acid Drug Dev.* 10(2): 63-75; Daniels, et al. (2002), *Anal. Biochem.* 305(2): 214-26; Chen, et al. (2003), *Proc. Natl. Acad. Sci. U.S.A.* 100(16): 9226-31; Khati, et al. (2003), *J. Virol.* 77(23): 12692-8; Vaish, et al. (2003), *Biochemistry* 42(29): 8842-51).

Aptamers can be created by an entirely in vitro selection process (Systematic Evaluation of Ligands by Experimental Enrichment, i.e., SELEX™) from libraries of random sequence oligonucleotides as described in U.S. Pat. Nos. 5,475,096 and 5,270,163. Aptamers have been generated against numerous proteins of therapeutic interest, including growth factors, enzymes, immunoglobulins, and receptors (Ellington and Szostak (1990), *Nature* 346(6287): 818-22; Tuerk and Gold (1990), *Science* 249 (4968): 505-510).

Aptamers have a number of attractive characteristics for use as therapeutics. In addition to high target affinity and specificity, aptamers have shown little or no toxicity or immunogenicity in standard assays (Wlotzka, et al. (2002), *Proc. Natl. Acad. Sci. U.S.A.* 99(13): 8898-902). Indeed, several therapeutic aptamers have been optimized and advanced through varying stages of pre-clinical development, including pharmacokinetic analysis, characterization of biological efficacy in cellular and animal disease models, and preliminary safety-pharmacology assessment (Reyderman and Stavchansky (1998), *Pharmaceutical Research* 15(6): 904-

10; Tucker et al., (1999), *J. Chromatography B*. 732: 203-212; Watson, et al. (2000), *Antisense Nucleic Acid Drug Dev.* 10(2): 63-75).

It is important that the pharmacokinetic properties for all oligonucleotide-based therapeutics, including aptamers, be tailored to match the desired pharmaceutical application. While aptamers directed against extracellular targets do not suffer from difficulties associated with intracellular delivery (as is the case with antisense and RNAi-based therapeutics), the aptamer must be distributed to target organs and tissues, and remain in the body (unmodified) for a period of time consistent with the desired dosing regimen. Early work on nucleic acid-based therapeutics has shown that, while unmodified oligonucleotides are degraded rapidly by nuclease digestion, protective modifications at the 2'-position of the sugar, and use of inverted terminal cap structures, e.g., [3'-3'dT], dramatically improve nucleic acid stability in vitro and in vivo (Green, et al. (1995), Chem. Biol. 2(10): 683-95; Jellinek, et al. (1995), Biochemistry 34(36): 11363-72; Ruckman, et al. (1998), J. Biol. Chem. 273(32): 20556-67; Uhlmann, et al. (2000), Methods Enzymol. 313: 268-84). In some SELEX selections (i.e., SELEX experiments or SELEX ions), starting pools of nucleic acids from which aptamers are selected are typically pre-stabilized through chemical modification, for example by incorporation of 2'-fluoropyrimidine (2'-F) substituted nucleotides, to enhance resistance of aptamers against nuclease attack. Aptamers incorporating 2'-O-methylpurine (2'-OMe purine) substituted nucleotides have also been developed through post-SELEX modification steps or, more recently, by enabling synthesis of 2'-OMe-containing random sequence libraries as an integral component of the SELEX process itself.

In addition to clearance by nucleases, oligonucleotide therapeutics are subject to elimination via renal filtration. As such, a nuclease-resistant oligonucleotide administered intravenously exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation to a PEG polymer ("PEGylation") can dramatically lengthen residence times of aptamers in circulation, thereby decreasing dosing frequency and enhancing effectiveness against targets. Previous work in animals has examined the plasma pharmacokinetic properties of PEG-conjugated aptamers (Reyderman and Stavchansky (1998), *Pharmaceutical Research* 15(6): 904-10; Watson, et al. (2000), *Antisense Nucleic Acid Drug Dev.* 10(2): 63-75)). Determining the extravasation of an aptamer therapeutic, including aptamer therapeutics conjugated to a modifying moiety or containing modified nucleotides and, in particular, determining the potential of aptamers or their modified forms to access diseased tissues (for example, sites of inflammation, or the interior of tumors) define the spectrum of therapeutic opportunities for aptamer intervention.

Typically, therapeutic aptamers are administered by injection, for example, by subcutaneous injection. Accordingly, the aptamer must be dissolved in a liquid vehicle for administration. The relatively high molecular weight of aptamers, and in particular aptamers that have been derivatized, for example by PEGylation, however, often makes it difficult to obtain a pharmaceutical composition wherein the aptamer is dissolved in a pharmaceutically acceptable solvent at a sufficient concentration to provide a pharmaceutical composition that is clinically useful for administration to an animal.

U.S. published application no. 2005/0175708 discloses a composition of matter that permits the sustained delivery of aptamers to a mammal. The aptamers are administered as microspheres that permit sustained release of the aptamers to the site of interest so that the aptamers can exert their biological activity over a prolonged period of time. The aptamers can be anti-VEGF aptamers.

P. Burmeister et al., (2004), *Chemistry and Biology:* 15, 25-33 disclose a method for generating a 2'-O-methyl aptamer (ARC245) that binds to vascular endothelial growth factor, which exhibits good stability.

Accordingly, there is a need in the art for improved pharmaceutical compositions, wherein the therapeutic agent is an aptamer. In particular, there is a need for pharmaceutical composition wherein the aptamer can be included in a pharmaceutically acceptable dosage form at a sufficient concentration to provide a pharmaceutical composition that is clinically useful for administration to an animal and that provides sustained- or controlled-release of the aptamer. The present invention addresses these needs as well as other needs.

Citation of any reference in this application is not to be construed as an admission that such reference is prior art to the present application.

5. SUMMARY OF THE INVENTION

These and other features and advantages of the present invention will become apparent from the remainder of the disclosure, in particular the following detailed description of the preferred embodiments, all of which illustrate by way of example the principles of the invention.

The invention relates to pharmaceutical compositions that comprise an aptamer or a pharmaceutically acceptable salt thereof. The pharmaceutical compositions are in the form of a gel. In one embodiment, the pharmaceutical compositions provide sustained- or controlled-release of the aptamer.

In one embodiment, the pharmaceutical compositions comprise a phospholipid or sphingomyelin; at least one organic solvent; and an aptamer, wherein the phospholipid or sphingomyelin and at least one organic solvent are present in amounts sufficient to form a gel.

In one embodiment, the pharmaceutical composition comprises a phospholipid; at least one organic solvent; and an aptamer, wherein the phospholipid and at least one organic solvent are present in amounts sufficient to form a gel.

In one embodiment, the pharmaceutical compositions comprise (i) a phospholipid or sphingomyelin; (ii) a polar aprotic organic solvent; (iii) a polar protic organic solvent; and (iv) an aptamer or a pharmaceutically acceptable salt thereof, wherein the phospholipid or sphingomyelin, polar aprotic organic solvent, and polar protic organic solvent are present in amounts sufficient to form a gel.

In one embodiment, the pharmaceutical compositions comprise (i) a phospholipid; (ii) a polar aprotic organic solvent; (iii) a polar protic organic solvent; and (iv) an aptamer or a pharmaceutically acceptable salt thereof, wherein the phospholipid, polar aprotic organic solvent, and polar protic organic solvent are present in amounts sufficient to form a gel.

In one embodiment, the pharmaceutical compositions comprise (i) a phospholipid or sphingomyelin, (ii) a solvent of selected from the group consisting of propylene glycol, glycerol formal, and mixtures thereof and (iii) an aptamer or a pharmaceutically acceptable salt thereof, wherein the phospholipid or sphingomyelin and the solvent selected from the group consisting of propylene glycol, glycerol formal, and mixtures thereof are present in amounts sufficient to form a gel. In one embodiment, the solvent is glycerol formal substantially free of other organic solvents. In one embodiment, the solvent is propylene glycol substantially free of other organic solvents. In one embodiment, the solvent is a mixture of propylene glycol substantially free of other organic solvents and glycerol formal substantially free of other organic solvents.

In one embodiment, the pharmaceutical compositions comprise (i) a phospholipid, (ii) a solvent of selected from the group consisting of propylene glycol, glycerol formal, and mixtures thereof and (iii) an aptamer or a pharmaceutically acceptable salt thereof, wherein the phospholipid or sphingomyelin and the solvent selected from the group consisting of propylene glycol, glycerol formal, and mixtures thereof are present in amounts sufficient to form a gel. In one embodiment, the solvent is glycerol formal substantially free of other organic solvents. In one embodiment, the solvent is propylene glycol substantially free of other organic solvents. In one embodiment, the solvent is a mixture of propylene glycol substantially free of other organic solvents and glycerol formal substantially free of other organic solvents.

In one embodiment, the pharmaceutical compositions comprise (i) a solvent comprising (a) a first solvent is selected from the group consisting of propylene glycol, glycerol formal, and mixtures thereof and (b) N-methyl pyrollidone; (ii) a phospholipid or sphingomyelin; and (iii) an aptamer or a pharmaceutically acceptable salt thereof, wherein the phospholipid or sphingomyelin and solvent are present in amounts sufficient to form a gel. In one embodiment, the first solvent is glycerol formal substantially free of other organic solvents. In one embodiment, the first solvent is propylene glycol substantially free of other organic solvents. In one embodiment, the first solvent is a mixture of propylene glycol substantially free of other organic solvents and glycerol formal substantially free of other organic solvents.

The invention further relates to a method of treating a condition in an animal comprising administering to an animal in need thereof a pharmaceutical composition of the invention.

6. BRIEF DESCRIPTION OF THE DRAWINGS

Not Applicable.

7. DETAILED DESCRIPTION OF THE INVENTION

The invention relates to pharmaceutical compositions that are a gel and comprise an aptamer. In one embodiment, the pharmaceutical compositions provide sustained- or controlled-release of the aptamer.

In one embodiment, the pharmaceutical composition comprises a phospholipid or sphingomyelin and at least one organic solvent; and an aptamer or a pharmaceutically acceptable salt thereof, wherein the phospholipid or sphingomyelin and at least one organic solvent are present in amounts sufficient to form of a gel.

In one embodiment, the pharmaceutical composition comprises a phospholipid; at least one organic solvent; and an aptamer or a pharmaceutically acceptable salt thereof, wherein the phospholipid and at least one organic solvent are present in amounts sufficient to form a gel.

In one embodiment, the pharmaceutical compositions comprise (i) a phospholipid or sphingomyelin; (ii) a polar aprotic organic solvent; (iii) a polar protic organic solvent; and (iv) an aptamer or a pharmaceutically acceptable salt thereof, wherein the phospholipid or sphingomyelin, polar aprotic organic solvent, and polar protic are present in amounts sufficient to form of a gel.

In one embodiment, the pharmaceutical compositions comprise (i) a phospholipid; (ii) a polar aprotic organic solvent; (iii) a polar protic organic solvent; and (iv) an aptamer or a pharmaceutically acceptable salt thereof, wherein the phospholipid, polar aprotic organic solvent, and polar protic are present in amounts sufficient to form of a gel.

In one embodiment, the pharmaceutical compositions comprise (i) a phospholipid or sphingomyelin, (ii) a solvent selected from the group consisting of propylene glycol substantially free of other organic solvents, glycerol formal substantially free of other organic solvents, and mixtures thereof and (iii) an aptamer or a pharmaceutically acceptable salt thereof, wherein the phospholipid or sphingomyelin and the solvent selected from the group consisting of propylene glycol substantially free of other organic solvents, glycerol formal substantially free of other organic solvents, and mixtures thereof are present in amounts sufficient to form of a gel. In one embodiment, the solvent is glycerol formal substantially free of other organic solvents. In one embodiment, the solvent is propylene glycol substantially free of other organic solvents. In one embodiment, the solvent is a mixture of glycerol formal substantially free of other organic solvents and propylene glycol substantially free of other organic solvents.

In one embodiment, the pharmaceutical compositions comprise (i) a phospholipid, (ii) a solvent of selected from the group consisting of propylene glycol substantially free of other organic solvents, glycerol formal substantially free of other organic solvents, and mixtures thereof and (iii) an aptamer or a pharmaceutically acceptable salt thereof, wherein the phospholipid and the solvent selected from the group consisting of propylene glycol substantially free of other organic solvents, glycerol formal substantially free of other organic solvents, and mixtures thereof are present in amounts sufficient to form of a gel. In one embodiment, the solvent is glycerol formal substantially free of other organic solvents. In one embodiment, the solvent is propylene glycol substantially free of other organic solvents. In one embodiment, the solvent is a mixture of glycerol formal substantially free of other organic solvents and propylene glycol substantially free of other organic solvents.

In one embodiment, the pharmaceutical compositions comprise (i) a solvent comprising (a) a first solvent is selected from the group consisting of propylene glycol substantially free of other organic solvents, glycerol formal substantially free of other organic solvents, and mixtures thereof and (b) N-methyl pyrollidone; (ii) a phospholipid or sphingomyelin; and (ii) an aptamer or a pharmaceutically acceptable salt thereof, wherein the phospholipid or sphingomyelin and solvent are present in amounts sufficient to form a gel. In one embodiment, the first solvent is glycerol formal substantially free of other organic solvents. In one embodiment, the first solvent is propylene glycol substantially free of other organic solvents. In one embodiment, the first solvent is a mixture of propylene glycol substantially free of other organic solvents and glycerol formal substantially free of other organic solvents.

In one embodiment, the pharmaceutical compositions comprise (i) a solvent comprising (a) a first solvent is selected from the group consisting of propylene glycol substantially free of other organic solvents, glycerol formal substantially free of other organic solvents, and mixtures thereof and (b) N-methyl pyrollidone; (ii) a phospholipid; and (ii) an aptamer or a pharmaceutically acceptable salt thereof, wherein the phospholipid and solvent are present in amounts sufficient to form a gel. In one embodiment, the first solvent is glycerol formal substantially free of other organic solvents. In one embodiment, the first solvent is propylene glycol substantially free of other organic solvents. In one embodiment, the first solvent is a mixture of propylene glycol substantially free of other organic solvents and glycerol formal substantially free of other organic solvents.

The invention further relates to a method of treating a condition in an animal comprising administering to an animal in need thereof a pharmaceutical composition of the invention.

7.1 Definitions

As used herein, the term "gel" means a material having an average viscosity of at least about 1,000 centipoise ("cP"), preferably at least about 2,000 cP, more preferably at least about 5,000 cP, even more preferably at least about 7,500 cP, and most preferably at least about 10,000 cP but less than about 100,000 cP, preferably less than about 75,000 cP at 20° C. Typically, a gel exhibits quiescent and/or dynamic interaction between its components, e.g., in the form of association complexes, which are generally reversible by application of force (e.g., shear) and/or temperature to achieve flow.

As used herein, the term "phospholipid" means a compound having the general formula:

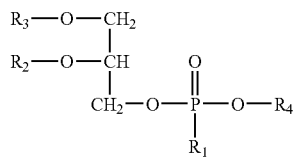

wherein
$R_1$ is —OH or —O$^-$;
$R_2$ is:
  (i) —H, or
  (ii) a $C_2$-$C_{36}$ saturated or unsaturated, linear or branched acyl group;
$R_3$ is:
  (i) —H,
  (ii) a $C_2$-$C_{36}$ saturated or unsaturated, linear or branched acyl group; or
  (iii) —C=C—$R_9$ wherein $R_9$ is a $C_1$-$C_{22}$ saturated or unsaturated, linear or branched hydrocarbon group, optionally substituted with one or more nitrogen containing groups;
and at least one of $R_2$ or $R_3$ is not —H;
$R_4$ is:
  (i) —H;
  (ii) —(CH$_2$)$_n$—$R_5$,
    wherein $R_5$ is —N($R_6$)($R_7$) or —N$^+$($R_6$)($R_7$)($R_8$),
    $R_6$, $R_7$, and $R_8$ are each independently —H, $C_1$-$C_3$ alkyl group, or $R_6$ and $R_7$ are connected to form a 5- or 6-membered heterocyclic ring with the nitrogen, and
    n is an integer ranging from 1 to 4, preferably 2;

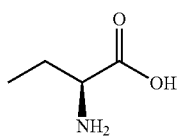

(iii)

-continued

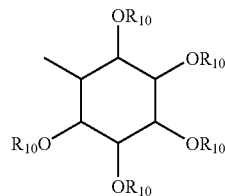

(iv)

wherein each $R_{10}$ is independently —H or —P(O)(OH)$_2$; or
  (v) —CH$_2$CH(OH)CH$_2$(OH).

As used herein, the term "saturated or unsaturated, linear or branched $C_2$-$C_{36}$ acyl group" means a group of formula —O—C(O)—R, wherein R is a $C_1$-$C_{35}$ hydrocarbon group that can be saturated or unsaturated, linear or branched.

As used herein, the term "sphingomyelin" means a compound having the general formula:

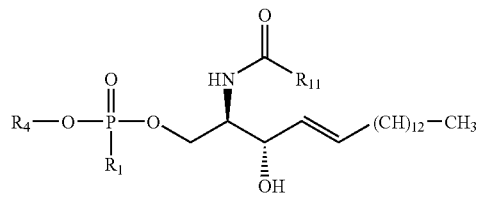

wherein
$R_1$ is —OH or —O$^-$;
$R_4$ is:
  (i) —H; or
  (i) —(CH$_2$)$_n$—$R_5$,
    wherein $R_5$ is —N($R_6$)($R_7$) or —N$^+$($R_6$)($R_7$)($R_8$),
    $R_6$, $R_7$, and $R_8$ are each independently —H, $C_1$-$C_3$ alkyl, or $R_6$ and $R_7$ are connected to form a 5- or 6-membered heterocyclic ring with the nitrogen, and
    n is an integer ranging from 1 to 4, preferably 2; and
  $R_{11}$ is a $C_1$-$C_{22}$ saturated or unsaturated, linear or branched hydrocarbon group optionally substituted with one or more nitrogen containing groups.

As used herein, the term "fatty acid" means a carboxylic acid of formula R—C(O)OH, wherein R is $C_6$-$C_{22}$ linear or branched, saturated or unsaturated, hydrocarbon group. Representative fatty acids include, but are not limited to, caproic acid, caprylic acid, capric acid, lauric acid, myristic acid, palmitic acid, stearic acid, palmic acid, palmitoleic acid, oleic acid, linoleic acid, and linolenic acid.

The term "polycarboxylic acid," as that term is used herein means a polymeric compound having more than one —C(O)OH group. One of ordinary skill in the art would readily recognize polymeric compounds that have more than one —C(O)OH group. Representative polycarboxylic acids include, but are not limited to, hyaluronic acid, polyglutamic acid, polyaspartic acid, and polyacrylic acid.

As used herein, the term "organic solvent" means any organic compound, or a mixture of organic compounds, that is a fluid at or above about 20° C., preferably at or above about 10° C., more preferably at or above about 0° C., most preferably at or above about –10° C. Typical organic solvents have a molecular weight of not more than about 500 g/mol and preferably not more than 100 g/mol. When organic solvents are administered to an animal, it is preferred that the organic solvents are compounds that do not significantly induce undue adverse effects such as excessive toxicity, irritation, or allergic response commensurate with a reasonable benefit/risk ratio (i.e., "pharmaceutically acceptable organic solvents").

As used herein, the term "polar aprotic organic solvent" means an organic solvent that has a dielectric constant greater than about 20, preferably greater than about 30, and more preferably greater than about 50, and does not include an —OH functional group.

As used herein, the term "polar protic organic solvent" means an organic solvent that has a dielectric constant greater than about 20, preferably greater than about 30, and more preferably greater than about 50, and includes an —OH functional group.

The term "aptamer," as used herein, means an oligonucleotide, which can be synthetic or natural, which can bind to a particular target molecule, such as a protein or metabolite, other than by Watson-Crick base pairing and have a pharmacological effect in an animal. Aptamers can be synthesized using conventional phosphodiester linked nucleotides and synthesized using standard solid or solution phase synthesis techniques which are known to those skilled in the art (See, for example, U.S. Pat. Nos. 5,475,096 and 5,270,163). The binding of aptamers to a target polypeptide can be readily tested by assays known to those skilled in the art.

Typically, the pharmacological effect is treating or preventing a condition in an animal.

The term "condition," as used herein means an interruption, cessation, or disorder of a bodily function, system, or organ. Representative conditions include, but are not limited to, diseases such as cancer, inflammation, diabetes, and organ failure.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human. In one embodiment, the animal is a mammal. In one embodiment, the animal is a human. In one embodiment, the animal is a canine, a feline, an equine, a bovine, an ovine, or a porcine.

The terms "effective amount" and "therapeutically effective amount," as used herein, mean an amount sufficient for treating or preventing or preventing a condition in an animal.

The phrases "treating," "treatment of," and the like, include the amelioration or cessation of a specified condition.

The phrases "preventing," "prevention of," and the like, include the avoidance of the onset of a condition.

The phrase "substantially free of," as used herein, means less than about 5 percent by weight. For example, the phrase "propylene glycol (or glycerol formal) substantially free of other organic solvents" means that the amount of other organic solvents in the propylene glycol (or glycerol formal) is less than about 5 percent by weight.

"$C_1$-$C_{22}$ hydrocarbon group" means a straight or branched, saturated or unsaturated, cyclic or non-cyclic, aromatic or non-aromatic, carbocyclic or heterocyclic group having from 1 to 22 carbon atoms. Similarly, phrases such as "$C_1$-$C_{22}$ hydrocarbon group," "$C_1$-$C_{16}$ hydrocarbon group," "$C_1$-$C_{10}$ hydrocarbon group," "$C_1$-$C_5$ hydrocarbon group," "$C_1$-$C_3$ hydrocarbon group," "$C_{16}$-$C_{22}$ hydrocarbon group," "$C_8$-$C_{18}$ hydrocarbon group," "$C_{10}$-$C_{18}$ hydrocarbon group," and "$C_{16}$-$C_{18}$ hydrocarbon group" means a straight or branched, saturated or unsaturated, cyclic or non-cyclic, aromatic or non-aromatic, carbocyclic or heterocyclic group having from 1 to 21 carbon atoms, from 1 to 16 carbon atoms, from 1 to 10 carbon atoms, from 1 to 5 carbon atoms, 1 to 3 carbon atoms, 16 to 22 carbon atoms, 8 to 18 carbon atoms, 10 to 18 carbon atoms, and 16 to 18 carbon atoms, respectively. Accordingly, the phrase "an acyl group of formula —C(O)—$R_1$, wherein $R_1$ is a $C_1$ to $C_{21}$ group means an acyl group of formula —C(O)—$R_1$, wherein $R_1$ is a straight or branched, saturated or unsaturated, cyclic or non-cyclic, aromatic or non-aromatic, carbocyclic or heterocyclic hydrocarbon group having from 1 to 21 carbon atoms. Representative acyl groups of formula —C(O)—$R_1$, wherein $R_1$ is an unsubstituted $C_1$ to $C_{21}$ group include, but are not limited to, acetyl, propanoyl, butanoyl, hexanoyl, caproyl, laurolyl, myristoyl, palmitoyl, stearoyl, palmioleoyl, oleoyl, linoleoyl, linolenoyl, and benzoyl.

The term "lower alkyl," as used herein means a $C_1$-$C_6$ hydrocarbon group.

The term "salt," as used herein, means two compounds that are not covalently bound but are chemically bound by ionic interactions.

The term "pharmaceutically acceptable," as used herein, when referring to a component of a pharmaceutical composition means that the component, when administered to an animal, does not have undue adverse effects such as excessive toxicity, irritation, or allergic response commensurate with a reasonable benefit/risk ratio. Accordingly, the term "pharmaceutically acceptable organic solvent," as used herein, means an organic solvent that when administered to an animal does not have undue adverse effects such as excessive toxicity, irritation, or allergic response commensurate with a reasonable benefit/risk ratio. Preferably, the pharmaceutically acceptable organic solvent is a solvent that is generally recognized as safe ("GRAS") by the United States Food and Drug Administration ("FDA"). Similarly, the term "pharmaceutically acceptable organic base," as used herein, means an organic base that when administered to an animal does not have undue adverse effects such as excessive toxicity, irritation, or allergic response commensurate with a reasonable benefit/risk ratio.

The phrase "injectable" or "injectable composition," as used herein, means a composition that can be drawn into a syringe and injected subcutaneously, intraperitoneally, or intramuscularly into an animal without causing adverse effects. Typically, a formulation or composition is considered to be injectable when no more than about 15%, preferably no more than about 10%, more preferably no more than about 5%, even more preferably no more than about 2%, and most preferably no more than about 1% of the formulation is retained on a 0.22 μm filter when the formulation is filtered through the filter at 98° F. In one embodiment, the term "injectable," as used herein, includes compositions that when warmed to a temperature of up to about 40° C. and then filtered through a 0.22 μm filter, no more than about 15%, preferably no more than about 10%, more preferably no more than about 5%, even more preferably no more than about 2%, and most preferably no more than about 1% of the formulation is retained on the filter. There are, however, some compositions of the invention, which are gels, that can be easily dispensed from a syringe but will be retained on a 0.22 μm filter. The term "injectable," as used herein, includes these gel compositions.

The phrase "drug depot," as used herein means a precipitate, which includes the aptamer, formed within the body of a treated animal that releases the aptamer over time to provide a pharmaceutically effective amount of the aptamer. A precipitate is an insoluble solid formed in a solvent at room temperature in vitro or in a physiological (in vivo) environment. The precipitate can take many forms such as, for example, a solid, a crystal, a gummy mass, or a gel. Preferably, the precipitate is a gummy mass or a gel.

The term "about," as used herein to describe a range of values, applies to both the upper limit and the lower limit of the range. For example, the phrase "ranges from about 90:10 to 10:90" has the same meaning as "ranges from about 90:10 to about 10:90."

7.2 The Gel

The pharmaceutical compositions of the invention are in the form of a gel. Without wishing to be bound be theory it is believed that the gel forms when the phospholipid or sphingomyelin are combined with the solvent in amounts sufficient to form a gel. Preferably the phospholipid or sphingomyelin are combined with the solvent with heating followed by cooling.

7.2.1 The Phospholipid

Any pharmaceutically acceptable phospholipid can be used in the pharmaceutical compositions of the invention.

Representative, pharmaceutically acceptable phospholipids include, but are not limited to:

phosphatidic acids of general formula:

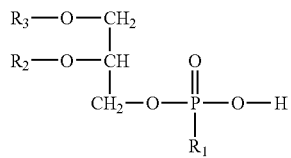

wherein $R_1$, $R_2$, and $R_3$ are defined above. Suitable phosphatidic acids suitable for use in the compositions and methods of the invention include, but are not limited to, the 1-acyl-2-acyl-sn-glycero-3-phosphates and the 1,2-diacyl-sn-glycero-3-phosphates commercially available from Avanti Polar Lipids Inc. of Alabaster, Ala.

phosphatidylethanolamines of general formula

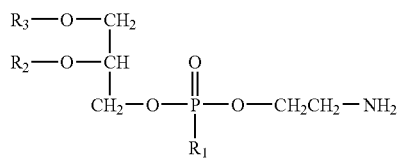

wherein $R_1$, $R_2$, and $R_3$ are defined above. Suitable phosphatidylethanolamines suitable for use in the compositions and methods of the invention include, but are not limited to, the 1-acyl-2-acyl-sn-glycero-3-phosphoethanolamines and the 1,2-diacyl-sn-glycero-3-phosphoethanolamines commercially available from Avanti Polar Lipids Inc. of Alabaster, Ala.

phosphatidylcholines of general formula

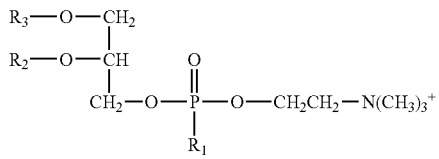

wherein $R_1$, $R_2$, and $R_3$ are defined above. Suitable phosphatidylcholines suitable for use in the compositions and methods of the invention include, but are not limited to, the 1-acyl-2-acyl-sn-glycero-3-phosphocholines, the 1,2-diacyl-sn-glycero-3-phosphoethanolamines (saturated series), and the 1,2-diacyl-sn-glycero-3-phosphoethanolamines (unsaturated series), commercially available from Avanti Polar Lipids Inc. of Alabaster, Ala. and Phospholipon®-50PG, Phospholipon®-53MCT, Phospholipon®-75SA, Phospholipon®-80, Phospholipon®-90NG, Phospholipon®-90H, and Phospholipon®-100H, commercially available from Phospholipid GmbH of Cologne, Germany. In one embodiment, the phospholipid is Phospholipon®-90H.

phosphatidylserines of general formula

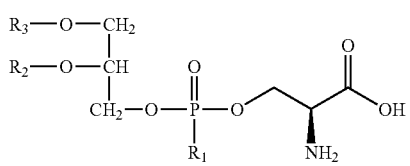

wherein $R_1$, $R_2$, and $R_3$ are defined above. Suitable phosphatidylserines suitable for use in the compositions and methods of the invention include, but are not limited to, the 1-acyl-2-acyl-sn-glycero-3-[phospho-L-serine]s and the 1,2-diacyl-sn-glycero-3-[phospho-L-serine]s commercially available from Avanti Polar Lipids Inc. of Alabaster, Ala.

plasmalogens of general formula

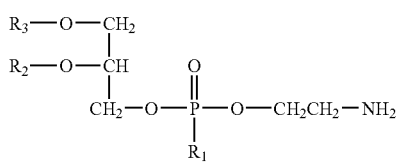

wherein $R_1$ and $R_2$ are defined above and $R_3$ is —C═C—$R_9$, wherein $R_9$ is defined above. Suitable plasmalogens suitable for use in the compositions and methods of the invention include, but are not limited to, C16(Plasm)-12:0 NBD PC, C16(Plasm)-18:1 PC, C16(Plasm)-20:4 PC, C16(Plasm)-22:6 PC, C16(Plasm)-18:1 PC, C16(Plasm)-20:4 PE, and C16(Plasm)-22:6 PE, commercially available from Avanti Polar Lipids Inc. of Alabaster, Ala.

phosphatidylglycerols of general formula

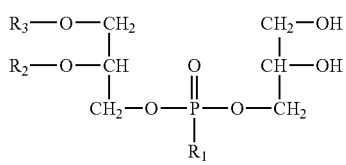

wherein $R_1$, $R_2$, and $R_3$ are defined above. Suitable phosphatidylglycerols suitable for use in the compositions and methods of the invention include, but are not limited to, the 1-acyl-2-acyl-sn-glycero-3-[phospho-rac-(1-glycerol)]s and the 1,2-diacyl-sn-glycero-3-[phospho-rac-(1-glycerol)]s, commercially available from Avanti Polar Lipids Inc. of Alabaster, Ala.

phosphatidylinositols of general formula

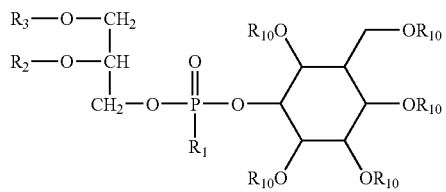

wherein $R_1$, $R_2$, $R_3$, and $R_{10}$ are defined above. Suitable phosphatidylinositols suitable for use in the compositions and methods of the invention include, but are not limited to, phosphatidylinositol, phosphatidylinositol-4-phosphate, and phosphatidylinositol-4,5-bisphosphate, commercially available from Avanti Polar Lipids Inc. of Alabaster, Ala.

The amount of phospholipid in the pharmaceutical composition typically ranges from about 0.1 percent to 10 percent by weight of the pharmaceutical composition.

In one embodiment, the amount of phospholipid in the pharmaceutical composition ranges from about 0.5 percent to 7 percent by weight of the pharmaceutical composition.

In one embodiment, the amount of phospholipid in the pharmaceutical composition ranges from about 1 percent to 4 percent by weight of the pharmaceutical composition.

In one embodiment, the amount of phospholipid in the pharmaceutical composition ranges from about 2 percent to 4 percent by weight of the pharmaceutical composition.

In one embodiment, the amount of phospholipid in the pharmaceutical composition is greater than about 1 percent by weight of the pharmaceutical composition.

In one embodiment, the amount of phospholipid in the pharmaceutical composition is greater than about 2 percent by weight of the pharmaceutical composition.

Typically, the greater the concentration of the phospholipid in the pharmaceutical composition the higher the viscosity of the pharmaceutical composition. Accordingly, it is possible to vary the viscosity of the pharmaceutical composition by varying the amount of the phospholipid present in the pharmaceutical composition.

One of ordinary skill in the art will recognize, however, that the amount of phospholipid present in the pharmaceutical compositions of the invention can vary widely depending on the organic solvents present, the aptamer present, and/or other additional components present in the pharmaceutical composition.

The phospholipids are commercially available or can be obtained by methods well known to those skilled in the art. Representative methods for obtaining phospholipids are described in Sandra Pesch et al., *Properties of Unusual Phospholipids Bearing Acetylenic Fatty Acids*, Tettrahedron, vol. 15, no. 43, 14627-14634 (1997); Sepp D. Kohlwein, *Phospholipid Synthesis, Sorting, Subcellular Traffic—The Yeast Approach*, Trends in Cell Biology, vol. 6, 260-266 (1996); Serguei V. Vinogradov, *Synthesis of Phospholipids—Oligodeoxyribonucleotide Conjugates*, Tett. Lett., vol. 36, no. 14, 2493-2496 (1995), and references cited therein.

7.2.2 The Sphingomyelin

Any pharmaceutically acceptable sphingomyelin can be used in the pharmaceutical compositions of the invention.

In one embodiment, the sphingomyelin is

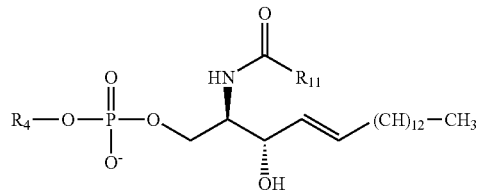

wherein $R_{11}$ is a $C_1$-$C_{24}$ linear, saturated or unsaturated hydrocarbon and $R_4$ is $-CH_2CH_2N(CH_3)_3^+$. In another embodiment, $R_{11}$ is a $C_8$-$C_{24}$ linear, saturated or unsaturated hydrocarbon and $R_4$ is $-CH_2CH_2N(CH_3)_3^+$. In another embodiment, $R_{11}$ is a $C_{16}$-$C_{24}$ linear, saturated or unsaturated hydrocarbon and $R_4$ is $-CH_2CH_2N(CH_3)_3^+$.

Suitable sphingomyelins include, but are not limited to, C2-Sphingomyelin, C6-Sphingomyelin, C18-Sphingomyelin, C6-NBD-Sphingomyelin, and C12-NBD Sphingomyelin, commercially available from Avant Polar Lipids Inc. of Alabaster, Ala.

The amount of sphingomyelin in the pharmaceutical composition typically ranges from about 0.1 percent to 10 percent by weight of the pharmaceutical composition.

In one embodiment, the amount of sphingomyelin in the pharmaceutical composition ranges from about 0.5 percent to 7 percent by weight of the pharmaceutical composition.

In one embodiment, the amount of sphingomyelin in the pharmaceutical composition ranges from about 1 percent to 4 percent by weight of the pharmaceutical composition.

In one embodiment, the amount of sphingomyelin in the pharmaceutical composition ranges from about 2 percent to 4 percent by weight of the pharmaceutical composition.

In one embodiment, the amount of sphingomyelin in the pharmaceutical composition is greater than about 1 percent by weight of the pharmaceutical composition.

In one embodiment, the amount of sphingomyelin in the pharmaceutical composition is greater than about 2 percent by weight of the pharmaceutical composition.

Typically, the greater the concentration of the sphingomyelin in the pharmaceutical composition the higher the viscosity of the pharmaceutical composition. Accordingly, it is possible to vary the viscosity of the pharmaceutical composition by varying the amount of the sphingomyelin present in the pharmaceutical composition.

One of ordinary skill in the art will recognize, however, that the amount of sphingomyelin present in the pharmaceutical compositions of the invention can vary widely depending on the organic solvents present, the aptamer present, and/or other additional components present in the pharmaceutical composition.

7.2.3. The Solvent

Any pharmaceutically acceptable organic solvent that forms a gel with a phospholipid or sphingomyelin can be used in the pharmaceutical compositions of the invention.

Suitable organic solvents can include small amounts of impurities. Typically, the organic solvents have a purity of greater than 95 percent by weight, preferably greater than 97 percent by weight, more preferably greater than 98 percent by weight, and most preferably greater than 99 percent by weight.

In one embodiment, the organic solvents are designated as GRAS ("generally recognized as safe") by the FDA for use or consumption by animals.

In another embodiment, the organic solvents are designated as GRAS by the FDA for use or consumption by humans.

In one embodiment, the solvent is a mixture of a first organic solvent and a second organic solvent. The first organic solvent and the second organic solvent, however, must be miscible.

In one embodiment, the first organic solvent is a polar aprotic solvent and the second organic solvent is a polar protic solvent.

Representative polar aprotic solvents useful in the compositions and methods of the invention include, but are not limited to, propylene carbonate, dimethyl sulfoxide (DMSO), dimethyl acetamide (DMA), dimethyl formamide (DMF), triacetin, and N-methyl-2-pyrrolidone (NMP).

Representative polar aprotic solvents useful in the compositions and methods of the invention include, but are not limited to, glycerol formal and diols such as propylene glycol, and 1,4-butanediol When the first organic solvent is a polar aprotic solvent and the second organic solvent is a polar protic solvent, the ratio of the first organic solvent to the second organic solvent can ranges from about 90:10 to 10:90. In one embodiment, the ratio of the first organic solvent to the second organic solvent ranges from about 80:20 to 20:80. In one embodiment, the ratio of the first organic solvent to the second organic solvent ranges from about 70:30 to 30:70. In one embodiment, the ratio of the first organic solvent to the second organic solvent ranges from about 60:40 to 40:60. In one embodiment, the ratio of the first organic solvent to the second organic solvent is about 50:50.

In one embodiment, the first organic solvent and the second organic solvent are each substantially free of water. In one embodiment, the first organic solvent and the second organic solvent each contain less than about 2 percent by weight of water. In one embodiment, the first organic solvent and the second organic solvent each contain less than about 1 percent by weight of water. In one embodiment, the first organic solvent and the second organic solvent each contain less than about 0.5 percent by weight of water. In one embodiment, the first organic solvent and the second organic solvent each contain less than about 0.2 percent by weight of water. Organic solvents that are substantially free of water are advantageous since they are not conducive to bacterial growth. Accordingly, it is typically not necessary to include a preservative in pharmaceutical compositions that are substantially free of water. However, in some embodiments, the non-aqueous pharmaceutical composition of the invention can contain a preservative. Another advantage of pharmaceutical compositions that use a pharmaceutically acceptable organic solvent as the solvent, preferably substantially free of water, is that hydrolysis of the aptamer is minimized. Typically, the more water present in the solvent the more readily the aptamer can be hydrolyzed. Accordingly, aptamer containing pharmaceutical compositions that use a pharmaceutically acceptable organic solvent as the solvent can be more stable than aptamer containing pharmaceutical compositions that use water as the solvent.

In one embodiment, the first organic solvent is propylene carbonate and the second organic solvent is glycerol formal.

In one embodiment, the first organic solvent is propylene carbonate and the second organic solvent is propylene glycol.

In one embodiment, the first organic solvent is propylene carbonate and the second organic solvent is glycerol formal glycol or propylene glycol and the ratio of the first organic solvent to the second organic solvent ranges from about 80:20 to about 20:80.

In one embodiment, the first organic solvent is propylene carbonate and the second organic solvent is glycerol formal or propylene glycol and the ratio of the first organic solvent to the second organic solvent ranges from about 75:25 to about 25:75.

In one embodiment, the first organic solvent is propylene carbonate and the second organic solvent is glycerol formal or propylene glycol and the ratio of the first organic solvent to the second organic solvent ranges from about 60:40 to about 40:60.

In one embodiment, the first organic solvent is propylene carbonate and the second organic solvent is glycerol formal or propylene glycol and the ratio of the first organic solvent to the second organic solvent ranges from about 50:50.

The total amount of organic solvent (i.e., the first organic solvent and the second organic solvent) in the pharmaceutical composition typically ranges from about 20 to about 99 percent by weight of the pharmaceutical composition.

In one embodiment, the total amount of organic solvent in the pharmaceutical composition is from about 35 to about 90 percent by weight of the pharmaceutical composition.

In one embodiment, the amount of organic solvent in the pharmaceutical composition is at least about 35 percent by weight of the pharmaceutical composition.

In one embodiment, the amount of organic solvent in the pharmaceutical composition is at least about 50 percent by weight of the pharmaceutical composition.

In one embodiment, the amount of organic solvent in the pharmaceutical composition is at least about 75 percent by weight of the pharmaceutical composition.

In one embodiment, the amount of organic solvent in the pharmaceutical composition is at least about 85 percent by weight of the pharmaceutical composition.

In one embodiment, the amount of organic solvent in the pharmaceutical composition is at least about 90 percent by weight of the pharmaceutical composition.

In another embodiment, the solvent is selected from the group consisting of propylene glycol substantially free of other organic solvents, glycerol formal substantially free of other organic solvents, and mixtures thereof.

Propylene glycol is an organic solvent represented by the formula:

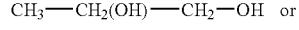

In one embodiment, the proplene glycol is 1,2-propylene glycol. In another embodiment, the propylene glycol is 1,3-propylene glycol. In one embodiment, the proplene glycol is a mixture of 1,2-propylene glycol and 1,3-propylene glycol.

Glycerol formal is an organic solvent of formula $C_4H_8O_3$ and exists as a mixture of 5-hydroxy-1,3-dioxane and 4-hydroxymethyl-1,3-dioxolane in a ratio of about 60:40. Although the solvent glycerol formal consists of two chemical compounds, the two chemical compounds being in a specific ratio of about 60:40, it is typically considered a "solvent" rather than a mixture of compounds. This is because the 5-hydroxy-1,3-dioxane and 4-hydroxymethyl-1,3-dioxolane are in equilibrium with each other. Accordingly, the term glycerol formal (i.e., a mixture of 5-hydroxy-1,3-dioxane and 4-hydroxymethyl-1,3-dioxolane in a ratio of about 60:40), as used herein, is an organic solvent substantially free of other organic solvents.

The propylene glycol and the glycerol formal can include small amounts of impurities. Typically, the propylene glycol and the glycerol formal each have a purity of greater than 95 percent by weight, preferably greater than 98 percent by weight, more preferably greater than 99 percent by weight. The solvent, especially glycerol formal, can include a stabilizer. Typically, the stabilizer is present in an amount of 0.5 weight percent or less, preferably an amount of 0.25 weight percent or less, and most preferably an amount of 0.5 weight percent or less. For example, commercially available glycerol formal typical contains ethylenediaminetetraacetate (EDTA), thiodipropionic acid, and propyl gallate as stabilizers.

In one embodiment, the propylene glycol and glycerol formal are each substantially free of water. In one embodiment, the propylene glycol and glycerol formal each contain less than about 2 percent by weight of water. In one embodiment, the propylene glycol and glycerol formal each contain less than about 1 percent by weight of water. In one embodiment, the propylene glycol and glycerol formal each contain less than about 0.5 percent by weight of water. In one embodiment, the propylene glycol and glycerol formal each contain less than about 0.2 percent by weight of water. Propylene glycol and glycerol formal substantially free of water is advantageous since they are not conducive to bacterial growth. Accordingly, it is typically not necessary to include a preservative in pharmaceutical compositions that are substantially free of water. However, in some embodiments, the non-aqueous pharmaceutical composition of the invention can contain a preservative.

In one embodiment, the pharmaceutical composition comprises a mixture of propylene glycol and glycerol formal. The ratio of propylene glycol to glycerol formal can range from about 2:98 to 98:2. In one embodiment, the ratio of propylene glycol to glycerol formal ranges from about 5:95 to 95:5. In one embodiment, the ratio of propylene glycol to glycerol formal ranges from about 10:90 to 90:10. In one embodiment, the ratio of propylene glycol to glycerol formal ranges from about 25:75 to 75:25. In one embodiment, the ratio of propylene glycol to glycerol formal ranges from about 55:45 to 45:55. In one embodiment, the ratio of propylene glycol to glycerol formal is about 50:50.

The amount of propylene glycol, glycerol formal, or mixture thereof in the pharmaceutical composition typically ranges from about 20 to about 99 percent by weight of the pharmaceutical composition.

In one embodiment, the amount of propylene glycol, glycerol formal, or mixture thereof in the pharmaceutical composition ranges from about 35 to about 90 percent by weight of the pharmaceutical composition.

In one embodiment, the amount of propylene glycol, glycerol formal, or mixture thereof in the pharmaceutical composition is at least about 35 percent by weight of the pharmaceutical composition.

In one embodiment, the amount of propylene glycol, glycerol formal, or mixture thereof in the pharmaceutical composition is at least about 50 percent by weight of the pharmaceutical composition.

In one embodiment, the amount of propylene glycol, glycerol formal, or mixture thereof in the pharmaceutical composition is at least about 75 percent by weight of the pharmaceutical composition.

In one embodiment, the amount of propylene glycol, glycerol formal, or mixture thereof in the pharmaceutical composition is at least about 85 percent by weight of the pharmaceutical composition.

In another embodiment, the solvent is a mixture of (i) a first organic solvent selected from the group consisting of propylene glycol, glycerol formal, and mixtures thereof and (ii) N-methyl pyrrolidone. In one embodiment, the solvent is a mixture of (i) a first organic solvent selected from the group consisting of propylene glycol substantially free of other organic solvents, glycerol formal substantially free of other organic solvents, and mixtures thereof and (ii) N-methyl pyrrolidone substantially free of other organic solvents.

The propylene glycol, glycerol formal, and N-methyl pyrrolidone can include small amounts of impurities. Typically, each of the propylene glycol, glycerol formal, and N-methyl pyrrolidone have a purity of greater than 95 percent by weight, preferably greater than 98 percent by weight, more preferably greater than 99 percent by weight. The solvent, especially glycerol formal, can include a stabilizer. Typically, the stabilizer is present in an amount of 0.5 weight percent or less, preferably an amount of 0.25 weight percent or less, and most preferably an amount of 0.5 weight percent or less.

In one embodiment, the propylene glycol, glycerol formal, and N-methyl pyrrolidone are each substantially free of water. In one embodiment, the propylene glycol, glycerol formal, and N-methyl pyrrolidone each contain less than about 2 percent by weight of water. In one embodiment, the propylene glycol, glycerol formal, and N-methyl pyrrolidone each contain less than about 1 percent by weight of water. In one embodiment, the propylene glycol, glycerol formal, and N-methyl pyrrolidone each contain less than about 0.5 percent by weight of water. In one embodiment, the propylene glycol, glycerol formal, and N-methyl pyrrolidone each contain less than about 0.2 percent by weight of water. Propylene glycol, glycerol formal, and N-methyl pyrrolidone substantially free of water are advantageous since they are not conducive to bacterial growth. Accordingly, it is typically not necessary to include a preservative in pharmaceutical compositions that are substantially free of water. However, in some embodiments, the non-aqueous pharmaceutical composition of the invention can contain a preservative.

The ratio of the propylene glycol, glycerol formal, or mixture thereof to the N-methyl pyrrolidone can range from about 2:98 to 98:2. In one embodiment, the ratio of the propylene glycol, glycerol formal, or mixture thereof to the N-methyl pyrrolidone ranges from about 5:95 to 95:5. In one embodiment, the ratio of the propylene glycol, glycerol formal, or mixture thereof to the N-methyl pyrrolidone ranges from about 10:90 to 90:10. In one embodiment, the ratio of the propylene glycol, glycerol formal, or mixture thereof to the N-methyl pyrrolidone ranges from about 25:75 to 75:25. In one embodiment, the ratio of the propylene glycol, glycerol formal, or mixture thereof to the N-methyl pyrrolidone ranges from about 55:45 to 45:55. In one embodiment, the ratio of the propylene glycol, glycerol formal, or mixture thereof to the N-methyl pyrrolidone is about 50:50.

The amount of propylene glycol, glycerol formal, and N-methyl pyrrolidone in the pharmaceutical composition typically ranges from about 20 to about 99 percent by weight of the pharmaceutical composition.

In one embodiment, the amount of propylene glycol, glycerol formal, and N-methyl pyrrolidone in the pharmaceutical composition ranges from about 35 to about 90 percent by weight of the pharmaceutical composition.

In one embodiment, the amount of propylene glycol, glycerol formal, and N-methyl pyrrolidone in the pharmaceutical composition is at least about 35 percent by weight of the pharmaceutical composition.

In one embodiment, the amount of propylene glycol, glycerol formal, and N-methyl pyrrolidone in the pharmaceutical composition is at least about 50 percent by weight of the pharmaceutical composition.

In one embodiment, the amount of propylene glycol, glycerol formal, and N-methyl pyrrolidone in the pharmaceutical composition is at least about 75 percent by weight of the pharmaceutical composition.

In one embodiment, the amount of propylene glycol, glycerol formal, and N-methyl pyrrolidone in the pharmaceutical composition is at least about 85 percent by weight of the pharmaceutical composition.

7.3 The Aptamer

The aptamer can be any aptamer known to those skilled in the art.

In one embodiment, the aptamer is a DNA strand. In one embodiment, the DNA is double stranded DNA. In one embodiment, the DNA is single stranded DNA.

In one embodiment, the aptamer is an RNA strand.

In one embodiment, the aptamer has a molecular weight of up to 80 kD. In one embodiment, the molecular weight of the aptamer ranges from about 15 kD to 80 Kd. In one embodiment, the molecular weight of the aptamer ranges from about 10 kD to 80 Kd. In one embodiment, the molecular weight of the aptamer ranges from about 5 kD to 80 Kd.

In one embodiment, the aptamer has a molecular weight of up to 60 kD. In one embodiment, the molecular weight of the aptamer ranges from about 15 kD to 60 Kd. In one embodiment, the molecular weight of the aptamer ranges from about 10 kD to 60 Kd. In one embodiment, the molecular weight of the aptamer ranges from about 5 kD to 60 Kd.

In one embodiment, the aptamer has a molecular weight of up to 40 kD. In one embodiment, the molecular weight of the aptamer ranges from about 15 kD to 40 Kd. In one embodiment, the molecular weight of the aptamer ranges from about 10 kD to 40 Kd. In one embodiment, the molecular weight of the aptamer ranges from about 5 kD to 40 Kd.

In one embodiment, the aptamer has a molecular weight of up to 30 kD. In one embodiment, the molecular weight of the aptamer ranges from about 15 kD to 30 Kd. In one embodiment, the molecular weight of the aptamer ranges from about 10 kD to 30 Kd. In one embodiment, the molecular weight of the aptamer ranges from about 5 kD to 30 Kd.

In one embodiment, the aptamer has a molecular weight of more than 20 kD. In one embodiment, the molecular weight of the aptamer ranges from about 10 kD to 20 Kd. In one embodiment, the molecular weight of the aptamer ranges from about 5 kD to 20 Kd.

In one embodiment, the molecular weight of the aptamer ranges from about 5 kD to 10 Kd.

The nucleotides that make up the aptamer can be modified to, for example, improve their stability, i.e., improve their in vivo half-life, and/or to reduce their rate of excretion when administered to an animal. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Modified nucleotides may also include 2' substituted sugars such as 2'-O-methyl-; 2'-O-alkyl; 2'-O-allyl; 2'-S-alkyl; 2'-S-allyl; 2'-fluoro-; 2'-halo or 2'-azido-ribose; carbocyclic sugar analogues; α-anomeric sugars; and epimeric sugars such as arabinose, xyloses or lyxoses, pyranose sugars, furanose sugars, and sedoheptulose.

Modified nucleotides are known in the art and include, but are not limited to, alkylated purines and/or pyrimidines; acylated purines and/or pyrimidines; or other heterocycles. These classes of pyrimidines and purines are known in the art and include, pseudoisocytosine; N4,N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; and 1-methylcytosine.

The aptamer can also be modified by replacing one or more phosphodiester linkages with alternative linking groups. Alternative linking groups include, but are not limited to embodiments wherein P(O)O is replaced by P(O)S, P(S)S, P(O)NR$_2$, P(O)R, P(O)OR', CO, or CH$_2$, wherein each R or R' is independently H or a substituted or unsubstituted C$_1$-C$_{20}$ alkyl. A preferred set of R substitutions for the P(O)NR$_2$ group are hydrogen and methoxyethyl. Linking groups are typically attached to each adjacent nucleotide through an —O— bond, but may be modified to include —N— or —S— bonds. Not all linkages in an oligomer need to be identical.

The aptamer can also be modified by conjugating the aptamer to a polymer, for example, to reduce the rate of excretion when administered to an animal. For example, the aptamer can be "PEGylated," i.e., conjugated to polyethylene glycol ("PEG"). In one embodiment, the PEG has an average molecular weight ranging from about 20 kD to 80 kD. Methods to conjugate an aptamer with a polymer, such PEG, are well known to those skilled in the art (See, e.g., Greg T. Hermanson, *Bioconjugate Techniques*, Academic Press, 1966)

As an example of a modified aptamer useful in the compositions and methods of the invention see P. Burmeister et al., *Direct In Vitro Selection of a 2'-O-methyl Aptamer to VEGF*, Chemistry and Biology, vol. 12, 25-33, January 2005.

In one embodiment, the aptamer is conjugated to a polymer.

In one embodiment, the aptamer is an RNA strand that has been conjugated to a polymer.

In one embodiment, the aptamer is an DNA strand that has been conjugated to a polymer.

In one embodiment, the aptamer is conjugated to PEG.

In one embodiment, the aptamer is an RNA strand that has been conjugated to PEG.

In one embodiment, the aptamer is an DNA strand that has been conjugated to PEG.

In one embodiment, the aptamer is a RNA strand wherein at least one of the 2'hydroxyls on the sugars that make up the aptamer are O-methylated.

In one embodiment, the aptamer is a RNA strand wherein at least one of the 2'hydroxyls on the sugars that make up the aptamer are O-methylated and wherein the RNA strand has been conjugated to a polymer.

In one embodiment, the aptamer is a RNA strand wherein at least one of the 2'hydroxyls on the nucleotides that make up the aptamer are O-methylated and wherein the RNA strand has been conjugated to PEG.

In one embodiment, the aptamer is an aptamer that binds to VEGF (vascular endothelial growth factor).

In one embodiment, the aptamer is ARC224 identified in P. Burmeister et al., *Direct In Vitro Selection of a 2'-O-methyl Aptamer to VEGF*, Chemistry and Biology, vol. 12, 25-33, January 2005.

In one embodiment, the aptamer is ARC245 identified in P. Burmeister et al., *Direct In Vitro Selection of a 2'-O-methyl Aptamer to VEGF*, Chemistry and Biology, vol. 12, 25-33, January 2005.

In one embodiment, the aptamer is ARC225 identified in P. Burmeister et al., *Direct In Vitro Selection of a 2'-O-methyl Aptamer to VEGF*, Chemistry and Biology, vol. 12, 25-33, January 2005.

In one embodiment, the aptamer is ARC259 identified in P. Burmeister et al., *Direct In Vitro Selection of a 2'-O-methyl Aptamer to VEGF*, Chemistry and Biology, vol. 12, 25-33, January 2005.

In one embodiment, the aptamer is ARC259 identified in P. Burmeister et al., *Direct In Vitro Selection of a 2'-O-methyl Aptamer to VEGF*, Chemistry and Biology, vol. 12, 25-33, January 2005 wherein the 5' phosphate group of the aptamer has been pegylated with:

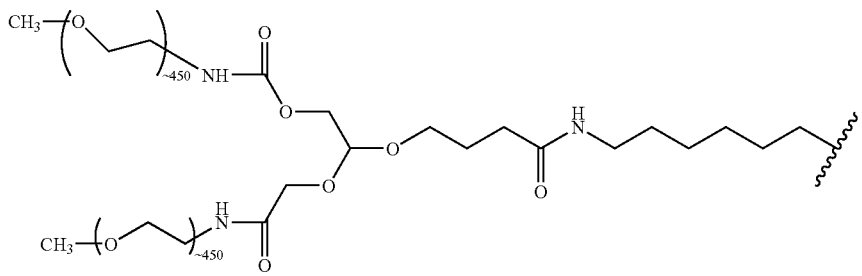

(referred to hereinafter as "PEGylated ARC259").

In one embodiment, at least some of the phosphate groups of the aptamer are protonated, i.e., the aptamer is present as the protonated aptamer. In one embodiment, all of the phosphate groups of the aptamer are protonated.

In one embodiment, the aptamer is a salt of the protonated aptamer. In one embodiment, the aptamer is an inorganic salt of the protonated aptamer. Suitable, inorganic salts include, but are not limited to, salts prepared by reacting the acidic phosphate groups of the protonated aptamer with a pharmaceutically acceptable inorganic base. Suitable inorganic bases include, but are not limited to, hydroxides of alkali metals such as sodium, potassium, and lithium; hydroxides of alkaline earth metal such as calcium and magnesium; and hydroxides of other metals, such as aluminum and zinc.

In one embodiment, the aptamer is present as an aptamer composition comprising the aptamer and one or more additional components. Representative embodiments wherein the aptamer is present as an aptamer composition comprising the aptamer and one or more additional components are provided below.

7.3.1. Compositions Comprising (i) a Pharmaceutically Acceptable Organic Base and (ii) a Protonated Aptamer In one embodiment, the aptamer is present as an aptamer composition comprising (i) a pharmaceutically acceptable organic base and (i) a protonated aptamer. Without wishing to be bound by theory, it is believed that the acidic phosphate groups of the protonated aptamer protonate the amine group of the pharmaceutically acceptable organic base to form a salt between one or more pharmaceutically acceptable organic base molecules and the aptamer as illustrated schematically below for a pharmaceutically acceptable organic base of formula Base-$NH_2$ and a protonated aptamer.

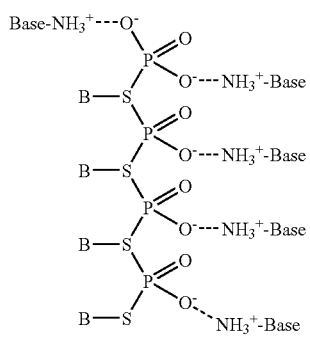

wherein B is a nucleotide, S is a sugar, and Base-$NH_3^+$ is a protonated pharmaceutically acceptable organic base. It is not necessary, however, that every phosphate group be ionically bound to a pharmaceutically acceptable organic base molecule.

Any pharmaceutically acceptable organic base known to those of ordinary skill in the art can be used in the pharmaceutical compositions of the invention. Representative organic bases include, but are not limited to, organic amines including, but not limited to, ammonia; unsubstituted or hydroxy-substituted mono-, di-, or tri-alkylamines such as cyclohexylamine, cyclopentylamine, cyclohexylamine, dicyclohexylamine; tributyl amine, N-methylamine, N-ethylamine, diethylamine; dimethylamine, triethylamine, mono-, bis-, or tris-(2-hydroxy-lower alkyl amines) (such as mono-, bis-, or tris-(2-hydroxyethyl)amine, 2-hydroxy-tert-butylamine, and tris-(hydroxymethyl)methylamine), N,N,-dilower alkyl-N-(hydroxy lower alkyl)-amines (such as N,N,-dimethyl-N-(2-hydroxyethyl)amine or N,N,-dialkyl-N-tris-(2-hydroxyethyl)amines)); pyridine; benzylamine; phenethylamine; N-methyl-D-glucamine; N,N'-dibenzylethylenediamine; chloroprocaine; choline; procaine, and amino acids such as arginine, lysine (See, also, Berge et al., *J. Pharm. Sci.*, 1977, 66, 1).

Any aptamer described herein can be used in the compositions.

The molar ratio of acidic groups on the protonated aptamer to basic groups on the a pharmaceutically acceptable organic base typically ranges from about 2:1 to 1:2. In one embodiment, the molar ratio of acidic groups on the protonated aptamer to basic groups on the pharmaceutically acceptable organic base ranges about 1.5:1 to 1:1.5. In one embodiment, the molar ratio of acidic groups on the protonated aptamer to basic groups on the pharmaceutically acceptable organic base ranges about 1.25:1 to 1:1.25. In one embodiment, the molar ratio of acidic groups on the protonated aptamer to basic groups on the pharmaceutically acceptable organic base ranges about 1.1:1. to 1:1.1. In one embodiment, the molar ratio of acidic groups on the protonated aptamer to basic groups on the pharmaceutically acceptable organic base is about 1:1. A wider range for the molar ratio of acidic groups on the protonated aptamer to basic groups on the pharmaceutically acceptable organic base, however, is also possible. For example, the molar ratio of acidic groups on the protonated aptamer to basic groups on the pharmaceutically acceptable organic base can range from about 15:1 to 1:15.

In one embodiment, the amine is an amino acid ester.

In one embodiment, the amine is an amino acid amide.

In one embodiment, the amine is a diamine (for example, N,N'-dibenzylethylenediamine or an ester or amide of lysine).

7.3.1.1. Compositions Comprising (i) an Amino Acid Ester or Amino Acid Amide and (ii) a Protonated Aptamer In one embodiment, the aptamer is present as a composition comprising (i) an amino acid ester or amide and (ii) a protonated aptamer. Without wishing to be bound by theory, it is believed that the acidic phosphate groups of the protonated aptamer protonate the amine group of the amino acid ester or amide to form a salt between one or more amino acid ester or amide molecules and the protonated aptamer as illustrated schematically below for an amino acid ester and a protonated aptamer:

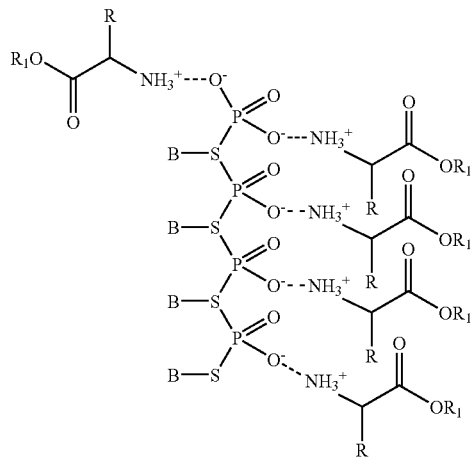

wherein B, S, R, and $R_1$ have the meaning described herein. It is not necessary, however, that every phosphate group be ionically bound to an amino acid ester or amino acid amide.

Any amino acid or amino acid ester described herein can be used in the compositions.

Any aptamer described herein can be used in the compositions.

The molar ratio of acidic groups on the protonated aptamer to basic groups on the amino acid ester or amino acid amide typically ranges from about 2:1 to 1:2. In one embodiment, the molar ratio of acidic groups on the protonated aptamer to basic groups on the amino acid ester or amino acid amide ranges about 1.5:1 to 1:1.5. In one embodiment, the molar ratio of acidic groups on the protonated aptamer to basic groups on the amino acid ester or amino acid amide ranges about 1.25:1 to 1:1.25. In one embodiment, the molar ratio of acidic groups on the protonated aptamer to basic groups on the amino acid ester or amino acid amide ranges about 1.1:1. to 1:1.1. In one embodiment, the molar ratio of acidic groups on the protonated aptamer to basic groups on the amino acid ester or amino acid amide is about 1:1. A wider range for the molar ratio of acidic groups on the protonated aptamer to basic groups on the amino acid ester or amino acid, however, is also possible. For example, the molar ratio of acidic groups on the protonated aptamer to basic groups on the amino acid ester or amino acid can range from about 15:1 to 1:15.

The Amino Acid Ester

The amino acid esters can be any ester of any amino acid, i.e., an amino acid wherein the carboxylic acid group of the amino acid is esterified with a $C_1$-$C_{22}$ alcohol. Accordingly, the amino acid esters have the general formula (I):

wherein

R is the amino acid side chain; and $R_1$ is a $C_1$ to $C_{22}$ hydrocarbon group.

As one of ordinary skill in the art would readily know, a wide variety of groups are possible for the amino acid side, R. For example, the amino acid side can be a hydrocarbon group that can be optionally substituted. Suitable substituents include, but are not limited to, halo, nitro, cyano, thiol, amino, hydroxy, carboxylic acid, sulfonic acid, aromatic group, and aromatic or non-aromatic heterocyclic group. Preferably the amino acid side chain is a $C_1$-$C_{10}$ straight or branched chain hydrocarbon, optionally substituted with a thiol, amino, hydroxy, carboxylic acid, aromatic group, or aromatic or non-aromatic heterocyclic group.

The amino acid ester can be an ester of a naturally occurring amino acid or a synthetically prepared amino acid. The amino acid can be a d-amino acid or an l-amino acid. Preferably, the amino acid ester is the ester of a naturally occurring amino acid. More, preferably, the amino acid ester is an ester of an amino acid selected from glycine, alanine, valine, leucine, isoleucine, pheylalanine, asparagine, glutamine, tryptophane, proline, serine, threonine, tyrosine, hydroxyproline, cysteine, methionine, aspartic acid, glutamic acid, lysine, arginine, and histidine.

The hydrocarbon group, $R_1$, can be any $C_1$ to $C_{22}$ hydrocarbon group. Representative $C_1$ to $C_{22}$ carbon groups include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, allyl, cyclopentyl, cyclohexyl, cis-9-hexadecenyl, cis-9-octadecenyl, cis, cis-9,12-octadecenyl, and cis, cis, cis-9,12,15-octadecatrienyl.

In one embodiment, $R_1$ is a straight chain hydrocarbon group.

In one embodiment, $R_1$ is a branched chain hydrocarbon group.

In one embodiment, $R_1$ is a saturated hydrocarbon group.

In one embodiment, $R_1$ is an unsaturated hydrocarbon group.

In one embodiment, $R_1$ is a straight chain, saturated hydrocarbon group.

In one embodiment, $R_1$ is a straight chain, unsaturated hydrocarbon group.

In one embodiment, $R_1$ is a $C_1$-$C_{16}$ hydrocarbon group.
In one embodiment, $R_1$ is a $C_1$-$C_{10}$ hydrocarbon group.
In one embodiment, $R_1$ is a $C_1$-$C_5$ hydrocarbon group.
In one embodiment, $R_1$ is a $C_1$-$C_3$ hydrocarbon group.
In one embodiment, $R_1$ is a $C_6$-$C_{22}$ hydrocarbon group.
In one embodiment, $R_1$ is a $C_6$-$C_{18}$ hydrocarbon group.
In one embodiment, $R_1$ is a $C_8$-$C_{18}$ hydrocarbon group.
In one embodiment, $R_1$ is a $C_{10}$-$C_{18}$ hydrocarbon group.
In one embodiment, $R_1$ is a $C_{16}$-$C_{18}$ hydrocarbon group.
In one embodiment, $R_1$ is a $C_{16}$-$C_{22}$ hydrocarbon group.
In one embodiment, $R_1$ is a $C_1$-$C_{16}$ straight chain hydrocarbon group.
In one embodiment, $R_1$ is a $C_1$-$C_{10}$ straight chain hydrocarbon group.
In one embodiment, $R_1$ is a $C_1$-$C_5$ straight chain hydrocarbon group.
In one embodiment, $R_1$ is a $C_1$-$C_3$ straight chain hydrocarbon group.
In one embodiment, $R_1$ is a $C_6$-$C_{22}$ straight chain hydrocarbon group.
In one embodiment, $R_1$ is a $C_6$-$C_{18}$ straight chain hydrocarbon group.
In one embodiment, $R_1$ is a $C_8$-$C_{18}$ straight chain hydrocarbon group.
In one embodiment, $R_1$ is a $C_{10}$-$C_{18}$ straight chain hydrocarbon group.
In one embodiment, $R_1$ is a $C_{16}$-$C_{18}$ straight chain hydrocarbon group.
In one embodiment, $R_1$ is a $C_{16}$-$C_{22}$ straight chain hydrocarbon group.
In one embodiment, $R_1$ is a $C_1$-$C_{16}$ branched chain hydrocarbon group.
In one embodiment, $R_1$ is a $C_1$-$C_{10}$ branched chain hydrocarbon group.
In one embodiment, $R_1$ is a $C_1$-$C_5$ branched chain hydrocarbon group.
In one embodiment, $R_1$ is a $C_1$-$C_3$ branched chain hydrocarbon group.
In one embodiment, $R_1$ is a $C_6$-$C_{22}$ branched chain hydrocarbon group.
In one embodiment, $R_1$ is a $C_6$-$C_{18}$ branched chain hydrocarbon group.
In one embodiment, $R_1$ is a $C_8$-$C_{18}$ branched chain hydrocarbon group.
In one embodiment, $R_1$ is a $C_{10}$-$C_{18}$ branched chain hydrocarbon group.
In one embodiment, $R_1$ is a $C_{16}$-$C_{18}$ branched chain hydrocarbon group.
In one embodiment, $R_1$ is a $C_{16}$-$C_{22}$ branched chain hydrocarbon group.
In one embodiment, $R_1$ is a $C_1$-$C_{16}$ straight chain unsaturated hydrocarbon group.
In one embodiment, $R_1$ is a $C_1$-$C_{10}$ straight chain unsaturated hydrocarbon group.
In one embodiment, $R_1$ is a $C_1$-$C_5$ straight chain unsaturated hydrocarbon group.
In one embodiment, $R_1$ is a $C_1$-$C_3$ straight chain unsaturated hydrocarbon group.
In one embodiment, $R_1$ is a $C_6$-$C_{22}$ straight chain unsaturated hydrocarbon group.
In one embodiment, $R_1$ is a $C_6$-$C_{18}$ straight chain unsaturated hydrocarbon group.
In one embodiment, $R_1$ is a $C_8$-$C_{18}$ straight chain unsaturated hydrocarbon group.
In one embodiment, $R_1$ is a $C_{10}$-$C_{18}$ straight chain unsaturated hydrocarbon group.
In one embodiment, $R_1$ is a $C_{16}$-$C_{18}$ straight chain unsaturated hydrocarbon group.
In one embodiment, $R_1$ is a $C_{16}$-$C_{22}$ straight chain unsaturated hydrocarbon group.

As discussed later, by varying the structure of $R_1$ it is possible to vary the properties of the pharmaceutical compositions.

The amino acid esters can be obtained by esterifying an amino acid with an alcohol of formula $R_1$—OH using methods well known to those skilled in the art such as those described in J. March, *Advanced Organic Chemistry, Reaction Mechanisms and Structure*, 4th ed. John Wiley & Sons, NY, 1992, pp. 393-400. The amino acids and alcohols of formula $R_1$—OH are commercially available or can be prepared by methods well known to those skilled in the art. When esterifying the amino acid with the alcohol of formula $R_1$—OH, it may be necessary to protect some other functional group of the amino acid or the alcohol with a protecting group that is subsequently removed after the esterification reaction. One of ordinary skill in the art would readily know what functional groups would need to be protected before esterifying the amino acid with the alcohol of formula $R_1$—OH. Suitable protecting groups are known to those skilled in the art such as those described in T. W. Greene, et al. *Protective Groups in Organic Synthesis*, 3rd ed. (1999).

The Amino Acid Amide

The amino acid amides can be any amide of any amino acid, i.e., an amino acid wherein the carboxylic acid group of the amino acid is reacted with an amine of formula $HN(R_3)(R_4)$, wherein $R_3$ and $R_4$ are defined above, to provide an amide. Accordingly, the amino acid amides have the general formula (II):

(II)

wherein
R is the amino acid side chain;
$R_3$ is a $C_1$ to $C_{22}$ hydrocarbon group; and
$R_4$ is hydrogen or a $C_1$ to $C_{22}$ hydrocarbon group.

As one of ordinary skill in the art would readily know, a wide variety of groups are possible for the amino acid side, R.

For example, the amino acid side can be a hydrocarbon group that can be optionally substituted. Suitable substituents include, but are not limited to, halo, nitro, cyano, thiol, amino, hydroxy, carboxylic acid, sulfonic acid, aromatic group, and aromatic or non-aromatic heterocyclic group. Preferably the amino acid side chain is a $C_1$-$C_{10}$ straight or branched chain hydrocarbon, optionally substituted with a thiol, amino, hydroxy, carboxylic acid, aromatic group, or aromatic or non-aromatic heterocyclic group; an aromatic group, or an aromatic or non-aromatic heterocyclic group.

The amino acid amide can be an amide of a naturally occurring amino acid or a synthetically prepared amino acid. The amino acid can be a d-amino acid or an l-amino acid. Preferably, the amino acid ester is the ester of a naturally occurring amino acid. More, preferably, the amino acid ester is an ester of an amino acid selected from glycine, alanine, valine, leucine, isoleucine, phenylalanine, asparagine, glutamine, tryptophane, proline, serine, threonine, tyrosine, hydroxyproline, cysteine, methionine, aspartic acid, glutamic acid, lysine, arginine, and histidine.

The $R_3$ group can be any $C_1$ to $C_{22}$ hydrocarbon group. The $R_4$ group can be hydrogen or any $C_1$ to $C_{22}$ hydrocarbon group. Representative $C_1$ to $C_{22}$ hydrocarbon groups include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, allyl, cyclopentyl, cyclohexyl, cis-9-hexadecenyl, cis-9-octadecenyl, cis, cis-9,12-octadecenyl, and cis, cis, cis-9,12,15-octadecatrienyl.

In one embodiment, $R_4$ is hydrogen and $R_3$ is a straight chain hydrocarbon group.

In one embodiment, $R_4$ is hydrogen and $R_3$ is a branched chain hydrocarbon group.

In one embodiment, $R_4$ is hydrogen and $R_3$ is a saturated hydrocarbon group.

In one embodiment, $R_4$ is hydrogen and $R_3$ is an unsaturated hydrocarbon group.

In one embodiment, $R_4$ is hydrogen and $R_3$ is a straight chain, saturated hydrocarbon group.

In one embodiment, $R_4$ is hydrogen and $R_3$ is a straight chain, unsaturated hydrocarbon group.

In one embodiment, $R_4$ is hydrogen and $R_3$ is a $C_1$-$C_{16}$ hydrocarbon group.

In one embodiment, $R_4$ is hydrogen and $R_3$ is a $C_1$-$C_{10}$ hydrocarbon group.

In one embodiment, $R_4$ is hydrogen and $R_3$ is a $C_1$-$C_5$ hydrocarbon group.

In one embodiment, $R_4$ is hydrogen and $R_3$ is a $C_1$-$C_3$ hydrocarbon group.

In one embodiment, $R_4$ is hydrogen and $R_3$ is a $C_6$-$C_{22}$ hydrocarbon group.

In one embodiment, $R_4$ is hydrogen and $R_3$ is a $C_6$-$C_{18}$ hydrocarbon group.

In one embodiment, $R_4$ is hydrogen and $R_3$ is a $C_8$-$C_{18}$ hydrocarbon group.

In one embodiment, $R_4$ is hydrogen and $R_3$ is a $C_{10}$-$C_{18}$ hydrocarbon group.

In one embodiment, $R_4$ is hydrogen and $R_3$ is a $C_{16}$-$C_{18}$ hydrocarbon group.

In one embodiment, $R_4$ is hydrogen and $R_3$ is a $C_{16}$-$C_{22}$ hydrocarbon group.

In one embodiment, $R_4$ is hydrogen and $R_3$ is a $C_1$-$C_{16}$ straight chain hydrocarbon group.

In one embodiment, $R_4$ is hydrogen and $R_3$ is a $C_1$-$C_{10}$ straight chain hydrocarbon group.

In one embodiment, $R_4$ is hydrogen and $R_3$ is a $C_1$-$C_5$ straight chain hydrocarbon group.

In one embodiment, $R_4$ is hydrogen and $R_3$ is a $C_1$-$C_3$ straight chain hydrocarbon group.

In one embodiment, $R_4$ is hydrogen and $R_3$ is a $C_6$-$C_{22}$ straight chain hydrocarbon group.

In one embodiment, $R_4$ is hydrogen and $R_3$ is a $C_6$-$C_{18}$ straight chain hydrocarbon group.

In one embodiment, $R_4$ is hydrogen and $R_3$ is a $C_8$-$C_{18}$ straight chain hydrocarbon group.

In one embodiment, $R_4$ is hydrogen and $R_3$ is a $C_{10}$-$C_{18}$ straight chain hydrocarbon group.

In one embodiment, $R_4$ is hydrogen and $R_3$ is a $C_{16}$-$C_{18}$ straight chain hydrocarbon group.

In one embodiment, $R_4$ is hydrogen and $R_3$ is a $C_{16}$-$C_{22}$ straight chain hydrocarbon group.

In one embodiment, $R_4$ is hydrogen and $R_3$ is a $C_1$-$C_{16}$ branched chain hydrocarbon group.

In one embodiment, $R_4$ is hydrogen and $R_3$ is a $C_1$-$C_{10}$ branched chain hydrocarbon group.

In one embodiment, $R_4$ is hydrogen and $R_3$ is a $C_1$-$C_5$ branched chain hydrocarbon group.

In one embodiment, $R_4$ is hydrogen and $R_3$ is a $C_1$-$C_3$ branched chain hydrocarbon group.

In one embodiment, $R_4$ is hydrogen and $R_3$ is a $C_6$-$C_{22}$ branched chain hydrocarbon group.

In one embodiment, $R_4$ is hydrogen and $R_3$ is a $C_6$-$C_{18}$ branched chain hydrocarbon group.

In one embodiment, $R_4$ is hydrogen and $R_3$ is a $C_8$-$C_{18}$ branched chain hydrocarbon group.

In one embodiment, $R_4$ is hydrogen and $R_3$ is a $C_{10}$-$C_{18}$ branched chain hydrocarbon group.

In one embodiment, $R_4$ is hydrogen and $R_3$ is a $C_{16}$-$C_{18}$ branched chain hydrocarbon group.

In one embodiment, $R_4$ is hydrogen and $R_3$ is a $C_{16}$-$C_{22}$ branched chain hydrocarbon group.

In one embodiment, $R_4$ is hydrogen and $R_3$ is a $C_1$-$C_{16}$ straight chain saturated hydrocarbon group.

In one embodiment, $R_4$ is hydrogen and $R_3$ is a $C_1$-$C_{10}$ straight chain saturated hydrocarbon group.

In one embodiment, $R_4$ is hydrogen and $R_3$ is a $C_1$-$C_5$ straight chain saturated hydrocarbon group.

In one embodiment, $R_4$ is hydrogen and $R_3$ is a $C_1$-$C_3$ straight chain saturated hydrocarbon group.

In one embodiment, $R_4$ is hydrogen and $R_3$ is a $C_6$-$C_{22}$ straight chain saturated hydrocarbon group.

In one embodiment, $R_4$ is hydrogen and $R_3$ is a $C_6$-$C_{18}$ straight chain saturated hydrocarbon group.

In one embodiment, $R_4$ is hydrogen and $R_3$ is a $C_8$-$C_{18}$ straight chain saturated hydrocarbon group.

In one embodiment, $R_4$ is hydrogen and $R_3$ is a $C_{10}$-$C_{18}$ straight chain saturated hydrocarbon group.

In one embodiment, $R_4$ is hydrogen and $R_3$ is a $C_{16}$-$C_{18}$ straight chain saturated hydrocarbon group.

In one embodiment, $R_4$ is hydrogen and $R_3$ is a $C_{16}$-$C_{22}$ straight chain saturated hydrocarbon group.

In one embodiment, each of $R_3$ and $R_4$ are a straight or branched chain, saturated or unsaturated hydrocarbon group, wherein $R_3$ and $R_4$ may be the same or different.

In one embodiment, each of $R_3$ and $R_4$ are a $C_1$-$C_{16}$ hydrocarbon group, wherein $R_3$ and $R_4$ may be the same or different.

In one embodiment, each of $R_3$ and $R_4$ are a $C_1$-$C_{10}$ hydrocarbon group, wherein $R_3$ and $R_4$ may be the same or different.

In one embodiment, each $R_3$ and $R_4$ are a $C_1$-$C_5$ hydrocarbon group, wherein $R_3$ and $R_4$ may be the same or different.

In one embodiment, each of $R_3$ and $R_4$ are a $C_1$-$C_3$ hydrocarbon group, wherein $R_3$ and $R_4$ may be the same or different.

In one embodiment, each of $R_3$ and $R_4$ are a $C_6$-$C_{22}$ hydrocarbon group, wherein $R_3$ and $R_4$ may be the same or different.

In one embodiment, each of $R_3$ and $R_4$ are a $C_6$-$C_{18}$ hydrocarbon group, wherein $R_3$ and $R_4$ may be the same or different.

In one embodiment, each of $R_3$ and $R_4$ are a $C_8$-$C_{18}$ hydrocarbon group, wherein $R_3$ and $R_4$ may be the same or different.

In one embodiment, each of $R_3$ and $R_4$ are a $C_{10}$-$C_{18}$ hydrocarbon group, wherein $R_3$ and $R_4$ may be the same or different.

In one embodiment, each of $R_3$ and $R_4$ are a $C_{16}$-$C_{18}$ hydrocarbon group, wherein $R_3$ and $R_4$ may be the same or different.

In one embodiment, each of $R_3$ and $R_4$ are a $C_{16}$-$C_{22}$ hydrocarbon group, wherein $R_3$ and $R_4$ may be the same or different.

In one embodiment, each of $R_3$ and $R_4$ are a $C_1$-$C_{16}$ straight chain hydrocarbon group, wherein $R_3$ and $R_4$ may be the same or different.

In one embodiment, each of $R_3$ and $R_4$ are a $C_1$-$C_{10}$ straight chain hydrocarbon group, wherein $R_3$ and $R_4$ may be the same or different.

In one embodiment, each of $R_3$ and $R_4$ are a $C_1$-$C_5$ straight chain hydrocarbon group, wherein $R_3$ and $R_4$ may be the same or different.

In one embodiment, each of $R_3$ and $R_4$ are a $C_1$-$C_3$ straight chain hydrocarbon group, wherein $R_3$ and $R_4$ may be the same or different.

In one embodiment, each of $R_3$ and $R_4$ are a $C_6$-$C_{22}$ straight chain hydrocarbon group, wherein $R_3$ and $R_4$ may be the same or different.

In one embodiment, each of $R_3$ and $R_4$ are a $C_6$-$C_{18}$ straight chain hydrocarbon group, wherein $R_3$ and $R_4$ may be the same or different.

In one embodiment, each of $R_3$ and $R_4$ are a $C_8$-$C_{18}$ straight chain hydrocarbon group, wherein $R_3$ and $R_4$ may be the same or different.

In one embodiment, each of $R_3$ and $R_4$ are a $C_{10}$-$C_{18}$ straight chain hydrocarbon group, wherein $R_3$ and $R_4$ may be the same or different.

In one embodiment, each of $R_3$ and $R_4$ are a $C_{16}$-$C_{18}$ straight chain hydrocarbon group, wherein $R_3$ and $R_4$ may be the same or different.

In one embodiment, each of $R_3$ and $R_4$ are a $C_{16}$-$C_{22}$ straight chain hydrocarbon group, wherein $R_3$ and $R_4$ may be the same or different.

In one embodiment, each of $R_3$ and $R_4$ are a $C_1$-$C_{16}$ branched chain hydrocarbon group, wherein $R_3$ and $R_4$ may be the same or different.

In one embodiment, each of $R_3$ and $R_4$ are a $C_1$-$C_{10}$ branched chain hydrocarbon group, wherein $R_3$ and $R_4$ may be the same or different.

In one embodiment, each of $R_3$ and $R_4$ are a $C_1$-$C_5$ branched chain hydrocarbon group, wherein $R_3$ and $R_4$ may be the same or different.

In one embodiment, each of $R_3$ and $R_4$ are a $C_1$-$C_3$ branched chain hydrocarbon group, wherein $R_3$ and $R_4$ may be the same or different.

In one embodiment, each of $R_3$ and $R_4$ are a $C_6$-$C_{22}$ branched chain hydrocarbon group, wherein $R_3$ and $R_4$ may be the same or different.

In one embodiment, each of $R_3$ and $R_4$ are a $C_6$-$C_{18}$ branched chain hydrocarbon group, wherein $R_3$ and $R_4$ may be the same or different.

In one embodiment, each of $R_3$ and $R_4$ are a $C_8$-$C_{18}$ branched chain hydrocarbon group, wherein $R_3$ and $R_4$ may be the same or different.

In one embodiment, each of $R_3$ and $R_4$ are a $C_{10}$-$C_{18}$ branched chain hydrocarbon group, wherein $R_3$ and $R_4$ may be the same or different.

In one embodiment, each of $R_3$ and $R_4$ are a $C_{16}$-$C_{18}$ branched chain hydrocarbon group, wherein $R_3$ and $R_4$ may be the same or different.

In one embodiment, each of $R_3$ and $R_4$ are a $C_{16}$-$C_{22}$ branched chain hydrocarbon group, wherein $R_3$ and $R_4$ may be the same or different.

In one embodiment, each of $R_3$ and $R_4$ are a $C_1$-$C_{16}$ straight chain saturated hydrocarbon group, wherein $R_3$ and $R_4$ may be the same or different.

In one embodiment, each of $R_3$ and $R_4$ are a $C_1$-$C_{10}$ straight chain saturated hydrocarbon group, wherein $R_3$ and $R_4$ may be the same or different.

In one embodiment, each of $R_3$ and $R_4$ are a $C_1$-$C_5$ straight chain saturated hydrocarbon group, wherein $R_3$ and $R_4$ may be the same or different.

In one embodiment, each of $R_3$ and $R_4$ are a $C_1$-$C_3$ straight chain saturated hydrocarbon group, wherein $R_3$ and $R_4$ may be the same or different.

In one embodiment, each of $R_3$ and $R_4$ are a $C_6$-$C_{22}$ straight chain saturated hydrocarbon group, wherein $R_3$ and $R_4$ may be the same or different.

In one embodiment, each of $R_3$ and $R_4$ are a $C_6$-$C_{18}$ straight chain saturated hydrocarbon group, wherein $R_3$ and $R_4$ may be the same or different.

In one embodiment, each of $R_3$ and $R_4$ are a $C_8$-$C_{18}$ straight chain saturated hydrocarbon group, wherein $R_3$ and $R_4$ may be the same or different.

In one embodiment, each of $R_3$ and $R_4$ are a $C_{10}$-$C_{18}$ straight chain saturated hydrocarbon group, wherein $R_3$ and $R_4$ may be the same or different.

In one embodiment, each of $R_3$ and $R_4$ are a $C_{16}$-$C_{18}$ straight chain saturated hydrocarbon group, wherein $R_3$ and $R_4$ may be the same or different.

In one embodiment, each of $R_3$ and $R_4$ are a $C_{16}$-$C_{22}$ straight chain saturated hydrocarbon group, wherein $R_3$ and $R_4$ may be the same or different.

In one embodiment, the combined number of carbon atoms in $R_3$ and $R_4$ is at least 6. In one embodiment, the combined number of carbon atoms in $R_3$ and $R_4$ is at least 8. In one embodiment, the combined number of carbon atoms in $R_3$ and $R_4$ is at least 10. In one embodiment, the combined number of carbon atoms in $R_3$ and $R_4$ is at least 12. In one embodiment, the combined number of carbon atoms in $R_3$ and $R_4$ is at least 18.

In one embodiment, the combined number of carbon atoms in $R_3$ and $R_4$ is less than 6. In one embodiment, the combined number of carbon atoms in $R_3$ and $R_4$ is less than 8. In one embodiment, the combined number of carbon atoms in $R_3$ and $R_4$ is less than 10. In one embodiment, the combined number of carbon atoms in $R_3$ and $R_4$ is less than 12. In one embodiment, the combined number of carbon atoms in $R_3$ and $R_4$ is less than 18.

In one embodiment, the combined number of carbon atoms in $R_3$ and $R_4$ ranges from about 1 to 16. In one embodiment, the combined number of carbon atoms in $R_3$ and $R_4$ ranges from about 1 to 10. In one embodiment, the combined number of carbon atoms in $R_3$ and $R_4$ ranges from about 1 to 5. In one embodiment, the combined number of carbon atoms in $R_3$ and $R_4$ ranges from about 1 to 3. In one embodiment, the combined number of carbon atoms in $R_3$ and $R_4$ ranges from about 16 to 22. In one embodiment, the combined number of carbon atoms in $R_3$ and $R_4$ ranges from about 16 to 18. In one embodiment, the combined number of carbon atoms in $R_3$ and $R_4$ ranges from about 8 to 18. In one embodiment, the combined number of carbon atoms in $R_3$ and $R_4$ ranges from about 10 to 18. In one embodiment, the combined number of carbon atoms in $R_3$ and $R_4$ ranges from about 12 to 18. In one embodiment, the combined number of carbon atoms in $R_3$ and $R_4$ ranges from about 6 to 30. In one embodiment, the combined number of carbon atoms in $R_3$ and $R_4$ ranges from about 22 to 30.

As discussed later, by varying the structure of $R_3$ and $R_4$ it is possible to vary the properties of the pharmaceutical compositions.

The amino acid amides can be obtained by converting the carboxylic acid group of the amino acid to an amide group using methods well known to those skilled in the art such as those described in J. March, *Advanced Organic Chemistry, Reaction Mechanisms and Structure,* 4th ed. John Wiley & Sons, NY, 1992, pp. 417-427. Typically, the amino acid is converted to an amino acid derivative such as an amino acid ester or an acid chloride of the amino acid and the amino acid derivative is then reacted with an amine of formula $NHR_3R_4$ to provide the amino acid amide. The amino acids and amines of formula $NHR_3R_4$ are commercially available or can be prepared by methods well known to those skilled in the art. When forming the derivative of the amino acid or reacting the amino acid derivative with an amine of formula $NHR_3R_4$, it may be necessary to protect some other functional group of the amino acid derivative or the amine with a protecting group that is subsequently removed after the amidation reaction. One of ordinary skill in the art would readily know what functional groups would need to be protected before reacting the derivative of the amino acid with the amine of formula $NHR_3R_4$. Suitable protecting groups are known to those skilled in the art such as those described in T. W. Greene, et al. *Protective Groups in Organic Synthesis,* 3rd ed. (1999).

7.3.1.1.a. Compositions wherein the Amino Acid Ester or Amide is an Amino Acid Ester or Amide of Lysine In one embodiment, the aptamer is present as a composition comprising (i) an ester or amide of lysine and (ii) a protonated aptamer.

In one embodiment, there is less than a molar equivalent of ester or amide of lysine molecules relative to acidic phosphate groups on the protonated aptamer, i.e., there is an excess of acidic phosphate groups on the protonated aptamer relative to amino acid ester or amide molecules.

Without wishing to be bound by theory it is believed that the amino acid ester or amide of lysine cross-links two protonated aptamer molecules as depicted below:

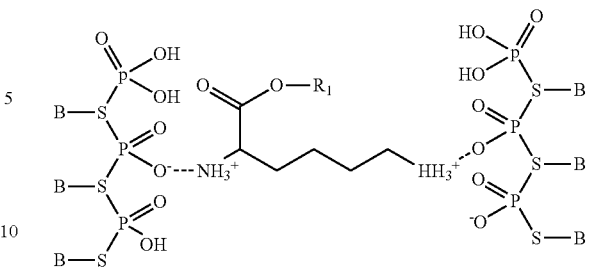

wherein B, S, and $R_1$ have the meaning described herein

The molar ratio of acidic groups on the protonated aptamer to basic groups on the ester or amide of lysine typically ranges from about 2:1 to 1:2. In one embodiment, the molar ratio of acidic groups on the protonated aptamer to basic groups on the ester or amide of lysine ranges about 1.5:1 to 1:1.5. In one embodiment, the molar ratio of acidic groups on the protonated aptamer to basic groups on the ester or amide of lysine ranges about 1.25:1 to 1:1.25. In one embodiment, the molar ratio of acidic groups on the protonated aptamer to basic groups on the ester or amide of lysine ranges about 1.1:1. to 1:1.1. In one embodiment, the molar ratio of acidic groups on the protonated aptamer to basic groups on the ester or amide of lysine is about 1:1. A wider range for the molar ratio of acidic groups on the protonated aptamer to basic groups on the ester or amide of lysine, however, is also possible. For example, the molar ratio of acidic groups on the protonated aptamer to basic groups on the ester or amide of lysine can range from about 15:1 to 1:15.

In other embodiments of the invention, the ester or amide of lysine is replaced with another diamine.

7.3.1.1.b. Compositions Comprising an Ester or Amide of Lysine, a Protonated Aptamer, and a Carboxylic Acid In one embodiment, the aptamer is present as a composition comprising (i) an ester or amide of lysine and (ii) a protonated aptamer and the composition further comprises a carboxylic acid. Without wishing to be bound by theory, it is believed that the carboxylic acid protonates the $\in$-amine group of lysine to provide a structure as depicted below:

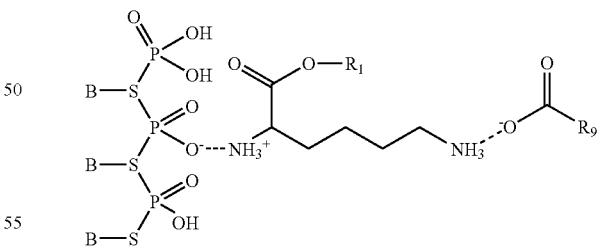

wherein B, S, and $R_1$ have the meaning described herein and $R_9$ is a $C_1$-$C_{21}$ hydrocarbon.

The combined molar ratio of acidic groups on the protonated aptamer and acid groups on the carboxylic acid to the amino acid ester or amino acid amide of lysine typically ranges from about 2:1 to 1:2. In one embodiment, the combined molar ratio of acidic groups on the protonated aptamer and acid groups on the carboxylic acid to the amino acid ester or amino acid amide of lysine ranges from about 1.5:1 to 1:1.5. In one embodiment, the combined molar ratio of acidic groups on the protonated aptamer and acid groups on the carboxylic acid to the amino acid ester or amino acid amide of lysine ranges from about 1.25:1 to 1:1.25. In one embodiment, the combined molar ratio of acidic groups on the protonated aptamer and acid groups on the carboxylic acid to the amino acid ester or amino acid amide of lysine ranges from about 1.1:1. to 1:1.1. In one embodiment, the combined molar ratio of acidic groups on the protonated aptamer and acid groups on the carboxylic acid to the amino acid ester or amino acid amide of lysine is about 1:1. A wider range for the molar ratio of acidic groups on the protonated aptamer and acid groups on the carboxylic acid to the amino acid ester or amino acid amide of lysine, however, is also possible. For example, the molar ratio of acidic groups on the protonated aptamer and acid groups on the carboxylic acid to the amino acid ester or amino acid amide of lysine can range from about 15:1 to 1:15.

Generally, the molar ratio of acidic groups on the protonated aptamer to acid groups on the carboxylic acid ranges from about 20:1 to 1:20. In one embodiment, the molar ratio of acidic groups on the protonated aptamer to acid groups on the carboxylic acid ranges from about 15:1 to 1:15. In one embodiment, the molar ratio of acidic groups on the protonated aptamer to acid groups on the carboxylic acid ranges from about 10:1 to 1:10. In one embodiment, the molar ratio of acidic groups on the protonated aptamer to acid groups on the carboxylic acid ranges from about 5:1 to 1:5. In one embodiment, the molar ratio of acidic groups on the protonated aptamer to acid groups on the carboxylic acid ranges from about 2:1 to 1:2.

The Carboxylic Acid

The carboxylic acid can be any pharmaceutically acceptable carboxylic acid. Typically, the carboxylic acid is a $C_1$-$C_{22}$ carboxylic acid. Suitable carboxylic acids include, but are not limited to, acetic acid, propanoic acid, butanoic acid, pentanoic acid, decanoic acid, hexanoic acid, benzoic acid, caproic acid, lauric acid, myristic acid, palmitic acid, stearic acid, palmic acid, oleic acid, linoleic acid, and linolenic acid.

In one embodiment, the carboxylic acid is a $C_1$-$C_{16}$ carboxylic acid.

In one embodiment, the carboxylic acid is a $C_1$-$C_{10}$ carboxylic acid.

In one embodiment, the carboxylic acid is a $C_1$-$C_5$ carboxylic acid.

In one embodiment, the carboxylic acid is a $C_1$-$C_3$ carboxylic acid.

In one embodiment, the carboxylic acid is a $C_6$-$C_{22}$ carboxylic acid.

In one embodiment, the carboxylic acid is a $C_6$-$C_{18}$ carboxylic acid.

In one embodiment, the carboxylic acid is a $C_8$-$C_{18}$ carboxylic acid.

In one embodiment, the carboxylic acid is a $C_{10}$-$C_{18}$ carboxylic acid.

In one embodiment, the carboxylic acid is a $C_6$-$C_{18}$ carboxylic acid.

In one embodiment, the carboxylic acid is a $C_{16}$-$C_{22}$ carboxylic acid.

In one embodiment, the carboxylic acid is a saturated or unsaturated fatty acid.

In one embodiment, the carboxylic acid is a saturated fatty acid.

In one embodiment, the carboxylic acid is an unsaturated fatty acid.

In one embodiment, the carboxylic acid is a dicarboxylic acid. Suitable dicarboxylic acids include, but are not limited to, oxalic acid, malonic aid, succinic acid, glutamic acid, adipic acid, and pimelic acid.

In one embodiment, the carboxylic acid is a polycarboxylic acid.

The carboxylic acids are commercially available or can be prepared by methods well known to those skilled in the art.

In one embodiment, the carboxylic acid is an N-acyl amino acid. The N-acyl amino acids have the following general formula (III):

wherein:

R is the amino acid side chain and is defined above; and $R_2$ is an acyl group of formula —C(O)—$R_5$, wherein $R_5$ is a substituted $C_1$ to $C_{21}$ hydrocarbon group, i.e., the acyl group, $R_2$, is a $C_1$- to $C_{22}$ acyl group. Representative acyl groups of formula —C(O)—$R_5$ include, but are not limited to, acetyl, propanoyl, butanoyl, hexanoyl, caproyl, heptoyl, octoyl, nonoyl, decoyl, undecoyl, dodecoyl, tridecoyl, tetradecoyl, pentadecoyl, hexadecoyl, heptadecoyl, octadecoyl, laurolyl, myristoyl, palmitoyl, stearoyl, palmioleoyl, oleoyl, linoleoyl, linolenoyl, and benzoyl.

In one embodiment, $R_5$ is a $C_1$-$C_{15}$ hydrocarbon group, i.e., the acyl group of formula —C(O)—$R_5$ is a $C_2$-$C_{16}$ acyl group.

In one embodiment, $R_5$ is a $C_1$-$C_9$ hydrocarbon group, i.e., the acyl group of formula —C(O)—$R_5$ is a $C_2$-$C_{10}$ acyl group.

In one embodiment, $R_5$ is a $C_1$-$C_5$ hydrocarbon group, i.e., the acyl group of formula —C(O)—$R_5$ is a $C_2$-$C_6$ acyl group.

In one embodiment, $R_5$ is a $C_1$-$C_3$ hydrocarbon group, i.e., the acyl group of formula —C(O)—$R_5$ is a $C_2$-$C_4$ acyl group.

In one embodiment, $R_5$ is a $C_5$-$C_{21}$ hydrocarbon group, i.e., the acyl group of formula —C(O)—$R_5$ is a $C_6$-$C_{22}$ acyl group.

In one embodiment, $R_5$ is a $C_5$-$C_{17}$ hydrocarbon group, i.e., the acyl group of formula —C(O)—$R_5$ is a $C_6$-$C_{18}$ acyl group.

In one embodiment, $R_5$ is a $C_7$-$C_{17}$ hydrocarbon group, i.e., the acyl group of formula —C(O)—$R_5$ is a $C_8$-$C_{18}$ acyl group.

In one embodiment, $R_5$ is a $C_9$-$C_{17}$ hydrocarbon group, i.e., the acyl group of formula —C(O)—$R_5$ is a $C_{10}$-$C_{18}$ acyl group.

In one embodiment, $R_5$ is a $C_{15}$-$C_{21}$ hydrocarbon group, i.e., the acyl group of formula —C(O)—$R_5$ is a $C_{16}$-$C_{22}$ acyl group.

In one embodiment, the acyl group of formula —C(O)—$R_5$ is obtained from a saturated or unsaturated fatty acid.

In one embodiment, the acyl group of formula —C(O)—$R_5$ is a caproyl, laurolyl, myristoyl, palmitoyl, stearoyl, palmioleoyl, oleoyl, linoleoyl, or linolenoyl group.

The N-acylated amino acids can be obtained by methods well known to those skilled in the art. For example, the N-acylated amino acids can be obtained by reacting an amino acid with an acid halide of formula T-C(O)—$R_5$, wherein T is a halide, preferably chloride, and $R_1$ is as defined above, using methods well known to those skilled in the art. When N-acylating the amino acid with the acid halide of formula T-C(O)—$R_5$, it may be necessary to protect some other functional group of the amino acid or the acid halide with a protecting group that is subsequently removed after the acylation reaction. One of ordinary skill in the art would readily know what functional groups would need to be protected before acylating the amino acid with the acid halide of formula T-C(O)—$R_5$. Suitable protecting groups are known to those skilled in the art such as those described in T. W. Greene, et al. *Protective Groups in Organic Synthesis,* 3rd ed. (1999).

Acid halides can be obtained using methods well known to those skilled in the art such as those described in J. March, *Advanced Organic Chemistry, Reaction Mechanisms and Structure,* 4th ed. John Wiley & Sons, NY, 1992, pp. 437-8. For example, acid halides can be prepared by reacting a carboxylic acid with thionyl chloride, bromide, or iodide. Acid chlorides and bromides can also be prepared by reacting a carboxylic acid with phosphorous trichloride or phosphorous tribromide, respectively. Acid chlorides can also be prepared by reacting a carboxylic acid with Ph3P in carbon tetrachloride. Acid fluorides can be prepared by reacting a carboxylic acid with cyanuric fluoride.

As discussed later, by varying the structure of carboxylic acid it is possible to vary the properties of the pharmaceutical compositions.

In other embodiments of the invention, the ester or amide of lysine is replaced with another diamine.

7.3.1.1.c. Compositions Comprising a Diester or Diamide of Aspartic Acid or Glutamic Acid and a Protonated Aptamer In another embodiment, the aptamer is present as a composition comprising (i) an ester or amide of aspartic acid or glutamic acid and (ii) a protonated aptamer and the side chain carboxylic acid group of the aspartic acid or glutamic acid is also esterified or amidated, i.e., a diester or diamide of aspartic acid or glutamic acid. Without wishing to be bound by theory it is believed that the acidic phosphate groups of the protonated aptamer protonate the amine group of the diester or diamide of aspartic acid or glutamic acid to form a salt between diester or diamide of aspartic acid or glutamic acid and the aptamer as illustrated below for a diester of aspartic acid that is protonated by a protonated aptamer to provide a structure as depicted below:

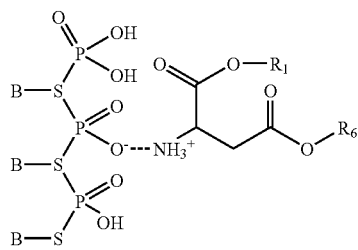

wherein B, S and $R_1$ are defined above and $R_6$ are defined below.

The diesters of aspartic acid and glutamic acid have the structures:

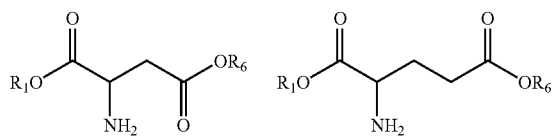

respectively, wherein $R_1$ is defined above and $R_6$ is the same as $R_1$. $R_1$ and $R_6$ can be the same or different. Typically, however, $R_1$ and $R_6$ are the same.

The diamides of aspartic acid and glutamic acid have the structures:

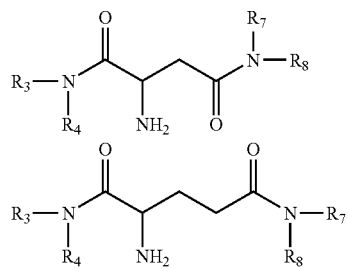

respectively, wherein $R_3$ and $R_4$ are defined above, $R_7$ is the same as $R_3$, and $R_8$ is the same as $R_4$. The amide groups —$N(R_3)(R_4)$ and —$N(R_7)(R_8)$ can be the same or different. Typically, however, the amide groups —$N(R_3)(R_4)$ and —$N(R_7)(R_8)$ are the same.

The molar ratio of acidic groups on the protonated aptamer to the diester or diamide of aspartic acid or glutamic acid typically ranges from about 2:1 to 1:2. In one embodiment, the molar ratio of acidic groups on the protonated aptamer to the diester or diamide of aspartic acid or glutamic acid ranges from about 1.5:1 to 1:1.5. In one embodiment, the molar ratio of acidic groups on the protonated aptamer to the diester or diamide of aspartic acid or glutamic acid ranges from about 1.25:1 to 1:1.25. In one embodiment, the molar ratio of acidic groups on the protonated aptamer to the diester or diamide of aspartic acid or glutamic acid ranges from about 1.1:1. to 1:1.1. In one embodiment, the molar ratio of acidic groups on the protonated aptamer to the diester or diamide of aspartic acid or glutamic acid is about 1:1. A wider range for molar ratio of acidic groups on the protonated aptamer to the diester or diamide of aspartic acid or glutamic acid, however, is also possible. For example, the molar ratio of acidic groups on the protonated aptamer to the diester or diamide of aspartic acid or glutamic acid can range from about 15:1 to 1:15.

7.3.2. Compositions Comprising (i) a Protonated Aptamer and (ii) a Polylysine In another embodiment, the aptamer is present as a composition comprising (i) a protonated aptamer and (ii) a polylysine.

Any of the aptamers described above can be used in the compositions.

Any polylysine (for example, any of the polylysines commercially available from Sigma-Aldrich of Milwaukee, Wis. as the hydrobromide salt, which can be converted to polylysine as described later) can be used in the pharmaceutical compositions. In one embodiment, the polylysine has a molecular weight range of from about 1,000 to 4,000. In one embodiment, the polylysine has a molecular weight range of from about 4,000 to 15,000. In one embodiment, the polylysine has a molecular weight range of from about 15,000 to 30,000. In one embodiment, the polylysine has a molecular weight range of from about 30,000 to 70,000. In one embodiment, the polylysine has a molecular weight range of from about 70,000 to 150,000. In one embodiment, the polylysine has a molecular weight range of from about 150,000 to 300,000.

Without wishing to be bound by theory, it is believed that the amine groups on the polylysine are protonated by acidic phosphate groups on the protonated aptamer.

Typically, the amount of polylysine relative to the amount of protonated aptamer is an amount sufficient to provide a solution of the composition (for example, a methanol or aqueous solution) having a pH value ranging from about 3 to 10. In one embodiment, a solution of the composition has a pH value ranging from about 5 to 9. In one embodiment, a solution of the composition has a pH value ranging from about 6 to 8. In one embodiment, a solution of the composition has a pH value of about 7. Other pH ranges, however, are also within the scope of the invention. For example, in one embodiment, a solution of the composition has a pH value ranging from about 3 to 7 and in another embodiment a solution of the composition has a pH value ranging from about 7 to 10.

The pH can be readily measured by dissolving the composition in a solvent (for example methanol or water) and removing a few microliters of the resulting solution and applying it to a wet pH test strip (such as commercially available from Sigma-Aldrich of Milwaukee, Wis.) that indicates the pH of the solution by the color of the test strip after the solution is applied.

7.3.3. Compositions Comprising (i) an Aptamer, (ii) a Divalent Metal Cation, and (iii) Optionally a Carboxylate In another embodiment, the aptamer is present as a composition comprising (i) the aptamer, (ii) a divalent metal cation and (iii) optionally a carboxylate. Without wishing to be bound by theory, it is believed that the divalent metal cation interacts with the phosphate groups on the aptamer to form a structure as depicted below:

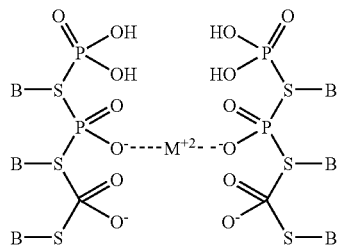

wherein $M^{+2}$ is a divalent metal cation and B and S are defined above.

Without wishing to be bound by theory, it is believed that when the composition includes the optional carboxylate, the divalent metal cation interacts with the phosphate groups on the aptamer and the carboxylate to form a structure as depicted below:

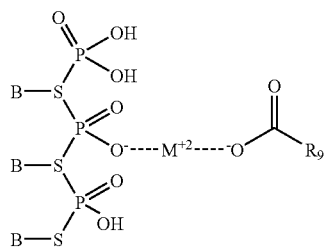

wherein B, S, $R_9$, and $M^{+2}$ are defined above. Without wishing to be bound by theory, it is believed that the structures are similar to the structures formed between an aptamer, the amino acid lysine, and a carboxylic acid, described above, except that the divalent metal cation replaces the protonated lysine.

Without wishing to be bound by theory it is also believed that when the composition includes the optional carboxylate, the divalent metal cation interacts with more than one carboxylate to form a structure as depicted below:

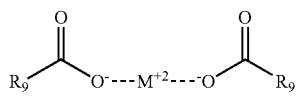

wherein $M^{+2}$ and $R_9$ are defined above.

Any of the aptamers described herein can be used in the compositions.

The carboxylate can be obtained from any pharmaceutically acceptable carboxylic acid. Any of the carboxylic acids described above can be used to provide the carboxylate.

In one embodiment, the carboxylate is obtained from an N-acyl amino acid of general formula (III). Any N-acyl amino acid of general formula (III) described herein can be used.

Suitable divalent metal cations include, but are not limited to, the alkaline earth metal cations, $Mg^{+2}$, $Zn^{+2}$, $Cu^{+2}$, and $Fe^{+2}$. Preferred divalent metal cations are $Ca^{+2}$, $Mg^{+2}$, $Zn^{+2}$, $Cu^{+2}$, and $Fe^{+2}$.

The combined molar ratio of anionic groups on the aptamer and anionic groups on the carboxylate to the divalent metal cation typically ranges from about 4:1 to 1:4. In one embodiment, the combined molar ratio of anionic groups on the aptamer and anionic groups on the carboxylate to the divalent metal cation ranges from about 3:1 to 1:3. In one embodiment, the combined molar ratio of anionic groups on the aptamer and anionic groups on the carboxylate to the divalent metal cation ranges from about 2.5:1 to 1:2.5. In one embodiment, the combined molar ratio of anionic groups on the aptamer and anionic groups on the carboxylate to the divalent metal cation ranges from about 2:1. to 1:2. In one embodiment, the combined molar ratio of anionic groups on the aptamer and anionic groups on the carboxylate to the divalent metal cation is about 2:1. A wider range for the molar ratio of anionic groups on the aptamer and anionic groups on the carboxylate to the divalent metal cation, however, is also possible. For example, the molar ratio of anionic groups on the aptamer and anionic groups on the carboxylate to the divalent metal cation can range from about 15:1 to 1:15.

Generally, the molar ratio of anionic groups on the aptamer to anionic groups on the carboxylate ranges from about 20:1 to 1:20. In one embodiment, the molar ratio of anionic groups on the aptamer to anionic groups on the carboxylate ranges from about 15:1 to 1:15. In one embodiment, the molar ratio of anionic groups on the aptamer to anionic groups on the carboxylate ranges from about 10:1 to 1:10. In one embodiment, the molar ratio of anionic groups on the aptamer to anionic groups on the carboxylate ranges from about 5:1 to 1:5. In one embodiment, the molar ratio of anionic groups on the aptamer to anionic groups on the carboxylate ranges from about 2:1 to 1:2.

7.3.4. General Properties of Aptamer Containing Compositions

By varying the lipophilicity and/or molecular weight of the amino acid ester or amino acid amide it is possible to vary the properties of the pharmaceutical compositions that include these components. The lipophilicity and/or molecular weight of the amino acid ester or amino acid amide can be varied by varying the amino acid and/or the alcohol (or amine) used to form the amino acid ester (or amino acid amide). For example, the lipophilicity and/or molecular weight of the amino acid ester can be varied by varying the $R_1$ hydrocarbon group of the amino acid ester. Typically, increasing the molecular weight of $R_1$ increase the lipophilicity of the amino acid ester. Similarly, the lipophilicity and/or molecular weight of the amino acid amide can be varied by varying the $R_3$ and/or $R_4$ groups of the amino acid amide.

Similarly, in pharmaceutical compositions that further comprise a carboxylic acid, it is possible to vary the properties of pharmaceutical compositions by varying the amount and/or lipophilicity and/or molecular weight of the carboxylic acid (i.e., by varying the lipophilicity or molecular weight of $R_9$ of the carboxylic acid). Similarly, in pharmaceutical compositions wherein the amino acid ester or amide is a diester or diamide of aspartic or glutamic acid, it is possible to vary the properties of pharmaceutical compositions by varying the amount and/or lipophilicity and/or molecular weight of the diester or diamide of aspartic or glutamic acid (i.e., by varying $R_1$ and/or $R_6$ of the diester of aspartic or glutamic acid or varying $R_3$, $R_4$, $R_7$ and/or $R_8$ of the diamide of aspartic or glutamic acid).

For example, by varying the lipophilicity and/or molecular weight of the amino acid ester or amino acid amide it is possible to vary the rate at which the aptamer is released from the pharmaceutical composition. Generally, the more lipophilic the amino acid ester or amino acid amide, the more slowly the aptamer is released from the pharmaceutical composition. Similarly, when the aptamer containing compositions further comprise a carboxylic acid or a diester or diamide of aspartic or glutamic acid, it is possible to vary the rate at which the aptamer is released from the pharmaceutical composition by varying the amount and/or lipophilicity and/or molecular weight of the carboxylic acid or diester or diamide of aspartic or glutamic acid.

Similarly, in pharmaceutical compositions that comprise an aptamer; a divalent metal cation; and a carboxylate, it is possible to vary the properties of pharmaceutical compositions (for example, the rate at which the aptamer is released from the pharmaceutical composition) by varying the amount and/or lipophilicity and/or molecular weight of the carboxylate (i.e., by varying the lipophilicity or molecular weight of $R_9$ of the carboxylate).

Release rates from a pharmaceutical composition can be measured injecting about 50 μL (50 μg) of the pharmaceutical composition into about 4 mL of deionized water in a centrifuge tube. The time that the pharmaceutical composition is injected into the water is recorded as T=0. After a specified amount of time, T, the sample is cooled to about −9° C. and spun on a centrifuge at about 13,000 rpm for about 20 min. The resulting supernatant is then analyzed by HPLC to determine the amount of aptamer present in the aqueous solution. The amount of aptamer in the pellet resulting from the centrifugation can also be determined by collecting the pellet, dissolving the pellet in about 10 μL of methanol, and analyzing the methanol solution by HPLC to determine the amount of aptamer in the precipitate. The amount of aptamer in the aqueous solution and the amount of aptamer in the precipitate are determined by comparing the peak area for the HPLC peak corresponding to the aptamer against a standard curve of aptamer peak area against concentration of aptamer. Suitable HPLC conditions can be readily determined by one of ordinary skill in the art.

7.3.5. Methods of Preparing the Aptamer Containing Compositions

The pharmaceutical compositions can be prepared by dissolving an inorganic salt of the aptamer, typically a potassium or sodium salt, in a solvent in which it is soluble, for example methanol or water, and adjusting the pH of the resulting solution to a value of between about 2 and 3 with an organic acid, such as formic acid, as depicted below:

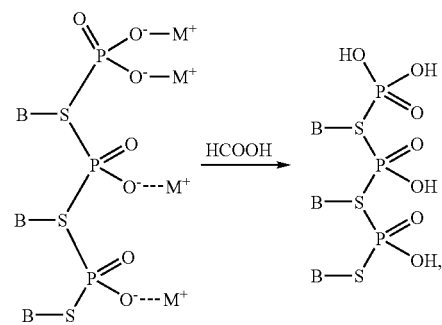

wherein S and B are defined above and $M^+$ is a metal ion, to provide a solution of the protonated aptamer.

The resulting solution of protonated aptamer is then dialyzed against water to remove excess formic acid and formate salts and if, for example, the neutralization is conducted in a methanol solvent, to replace the methanol with water. The water can then be removed from the aqueous solution of the protonated aptamer by lyophilization to provide the protonated aptamer or, alternatively, the aqueous solution of the protonated aptamer can be dialyzed against methanol to replace the water with methanol and then simply removing the methanol under reduced pressure to provide the protonated aptamer.

A solution of the protonated aptamer can also be prepared using a cation exchange resin. Any cationion exchange resin known to one skilled in the art can be used, for example, a Strata® SCX cation exchange resin (commercially available from Phenomenex of Torrance, Calif.) or a DOWEX® cation exchange resin, such as DOWEX® 50 (commercially available from Dow Chemical Company of Midland, Mich.) can be used. Typically, a column containing the cation exchange resin is first washed with an acidic solution to protonate the resin and then a solution of the inorganic salt of the aptamer, typically a potassium or sodium salt, in a solvent, for example methanol or water, is passed through the resin to provide, as the eluant, a solution of the protonated aptamer.

To prepare the aptamer compositions comprising an aptamer and an a pharmaceutically acceptable organic base (using an amino acid ester or amide as a representative pharmaceutically acceptable organic base), the protonated aptamer is dissolved in a solvent, such as methanol, typically with stirring, and to the resulting solution is then added the amino acid ester or amide, as depicted below:

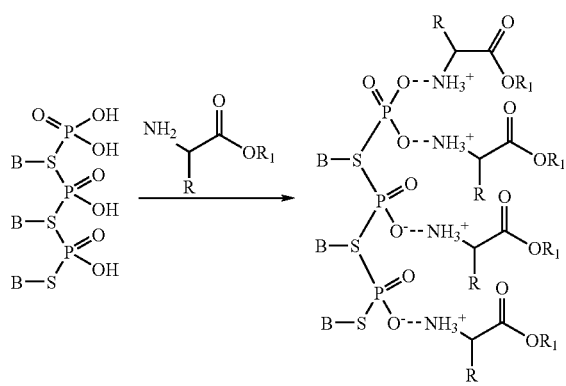

wherein S, B, R, and $R_1$ are defined above.

Any other components of the composition, such as a carboxylic acid, are then added to the resulting solution.

Typically, sufficient amino acid ester or amide, and any other components, are added to provide a solution having a pH value ranging from about 5 to 9. In one embodiment, sufficient amino acid ester or amide, and any other components, are added to provide a solution having a pH value ranging from about 6 to 8. In one embodiment, sufficient amino acid ester or amide, and any other components, are added to provide a solution having a pH value of about 7. The pH can be readily measured by removing a few microliters of the solution and applying it to a wet pH test strip (such as commercially available from Sigma-Aldrich of Milwaukee, Wis.) that indicates the pH of the solution by the color of the test strip after the solution is applied. The solvent is then removed under reduced pressure to provide the composition comprising the amino acid ester or amino acid amide and the aptamer.

To prepare the aptamer compositions comprising an aptamer; a divalent metal cation; and a carboxylate, the protonated aptamer is dissolved in a solvent, such as methanol, and to the resulting solution is added a metal salt, such as a metal acetate, or a metal hydroxide, preferably with stirring. To the resulting solution is then added the carboxylic acid, preferably with stirring. The solvent is then removed under reduced pressure to provide the aptamer composition comprising the aptamer, a divalent metal cation, and a carboxylate.

To prepare the aptamer compositions comprising an aptamer and polylysine, a polylysine solution (such as a methanol solution) is slowly added to a solution (such as a methanol solution) of the protonated aptamer, preferably with stirring, and the pH of the resulting solution monitored to provide a solution having the desired pH value. The methanol is then removed under reduced pressure to provide the aptamer composition comprising an aptamer and polylysine.

The polylysine is obtained from commercially available polylysine hydrobromide (commercially available from Sigma-Aldrich, St. Louis, Mo.) by simply neutralizing a solution (such as a methanol or water solution) of the polylysine hydrobromide with ammonium hydroxide to provide a solution having a pH value ranging from about 10 to 12. The resulting solution of polylysine is then dialyzed against water to remove excess ammonium bromide and ammonium hydroxide and if, for example, the neutralization is conducted in a methanol solvent, to replace the methanol with water. The water can then be removed from the aqueous solution of the polylysine by lyophilization to provide the polylysine or, alternatively, the aqueous solution of the polylysine can be dialyzed against methanol to replace the water with methanol and then the methanol simply removed under reduced pressure to provide the polylysine.

7.4 The Pharmaceutical Compositions

Any aptamer described herein can be used in the pharmaceutical compositions.

Any phospholipid or sphingomyelin described herein can be used in the pharmaceutical compositions.

Any of the solvents described herein can be used in the pharmaceutical compositions.

In one embodiment, the concentration of the aptamer in the pharmaceutical composition is greater than about 2 percent by weight of the pharmaceutical composition. In one embodiment, the concentration of the aptamer in the pharmaceutical composition is greater than about 5 percent by weight of the pharmaceutical composition. In one embodiment, the concentration of the aptamer in the pharmaceutical composition is greater than about 7.5 percent by weight of the pharmaceutical composition. In one embodiment, the concentration of the aptamer in the pharmaceutical composition is greater than about 10 percent by weight of the pharmaceutical composition. In one embodiment, the concentration of the aptamer in the pharmaceutical composition is greater than about 12 percent by weight of the pharmaceutical composition. In one embodiment, the concentration of the aptamer in the pharmaceutical composition is greater than about 15 percent by weight of the pharmaceutical composition. In one embodiment, the concentration of the aptamer in the pharmaceutical composition is ranges from about 2 percent to 5 percent by weight of the pharmaceutical composition. In one embodiment, the concentration of the aptamer in the pharmaceutical composition is ranges from about 2 percent to 7.5 percent by weight of the pharmaceutical composition. In one embodiment, the concentration of the aptamer in the pharmaceutical composition ranges from about 2 percent to 10 percent by weight of the pharmaceutical composition. In one embodiment, the concentration of the aptamer in the pharmaceutical composition is ranges from about 2 percent to 12 percent by weight of the pharmaceutical composition. In one embodiment, the concentration of the aptamer in the pharmaceutical composition is ranges from about 2 percent to 15 percent by weight of the pharmaceutical composition. In one embodiment, the concentration of the aptamer in the pharmaceutical composition is ranges from about 2 percent to 20 percent by weight of the pharmaceutical composition.

In one embodiment, the pharmaceutical composition has a viscosity of greater than about 1,000 cP at 20° C.

In one embodiment, the pharmaceutical composition has a viscosity of greater than about 2,000 cP at 20° C.

In one embodiment, the pharmaceutical composition has a viscosity of greater than about 5,000 cP at 20° C.

In one embodiment, the pharmaceutical composition has a viscosity of greater than about 10,000 cP at 20° C.

In one embodiment, the pharmaceutical composition has a viscosity of greater than about 15,000 cP at 20° C.

In one embodiment, the pharmaceutical composition has a viscosity of greater than about 20,000 cP at 20° C.

In one embodiment, the pharmaceutical composition has a viscosity of greater than about 25,000 cP at 20° C.

Typically, the pharmaceutical composition has a viscosity of less than about 100,000 cP at 20° C.

In one embodiment, the pharmaceutical composition has a viscosity of less than about 75,000 cP at 20° C.

In one embodiment, the pharmaceutical composition has a viscosity that ranges from about 1,000 cP to 100,000 cP at 20° C.

In one embodiment, the pharmaceutical composition has a viscosity that ranges from about 2,000 cP to 100,000 cP at 20° C.

In one embodiment, the pharmaceutical composition has a viscosity that ranges from about 5,000 cP to 100,000 cP at 20° C.

In one embodiment, the pharmaceutical composition has a viscosity that ranges from about 10,000 cP to 100,000 cP at 20° C.

In one embodiment, the pharmaceutical composition has a viscosity that ranges from about to 100,000 cP at 20° C.

In one embodiment, the pharmaceutical composition has a viscosity that ranges from about to 100,000 cP at 20° C.

In one embodiment, the pharmaceutical composition has a viscosity that ranges from about to 75,000 cP at 20° C.

In one embodiment, the pharmaceutical composition has a viscosity that ranges from about to 75,000 cP at 20° C.

In one embodiment, the pharmaceutical composition has a viscosity that ranges from about to 75,000 cP at 20° C.

In one embodiment, the pharmaceutical composition has a viscosity that ranges from about to 75,000 cP at 20° C.

In one embodiment, the pharmaceutical composition has a viscosity that ranges from about to 75,000 cP at 20° C.

In one embodiment, the pharmaceutical composition has a viscosity that ranges from about to 75,000 cP at 20° C.

In one embodiment, the pharmaceutical composition has a viscosity that ranges from about to 75,000 cP at 20° C.

In one embodiment, the pharmaceutical composition has a viscosity that ranges from about to 25,000 cP at 20° C.

In one embodiment, the pharmaceutical composition has a viscosity that ranges from about to 25,000 cP at 20° C.

In one embodiment, the pharmaceutical composition has a viscosity that ranges from about to 18,000 cP at 20° C.

In one embodiment, the pharmaceutical composition has a viscosity that ranges from about to 18,000 cP at 20° C.

In one embodiment, the pharmaceutical composition has a viscosity that is less than about 2,000 cP at 20° C.

Viscosity is determined using a Brookfield DV-II-PRO viscometer (commercially available from Brookfield of Marlboro, Mass.) with a cone and plate sampler, a CPE-40 spindle, a sample size of 0.5 mL, a speed of 3 rpm, and a temperature controlled to be 25° C.

In one embodiment, the pharmaceutical compositions can be expelled through an 18 to 24 gauge needle and therefore can be administered by injection.

7.4.1 Optional Additives

The present pharmaceutical compositions can optionally comprise a suitable amount of a pharmaceutically acceptable preservative, if desired, so as to provide additional protection against microbial growth.

Examples of preservatives useful in the pharmaceutical compositions of the invention include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chlorides (e.g., benzethonium chloride).

In one embodiment, the pharmaceutical compositions of the invention can optionally contain a suitable amount of a pharmaceutically acceptable polymer. The polymer further increases the viscosity of the pharmaceutical composition. Many of the pharmaceutical compositions of the invention lose their gel properties at temperatures greater than about 40° C. By including a polymer in the pharmaceutical compositions, the pharmaceutical compositions maintain their gel properties at higher temperatures.

Suitable polymers for use in the compositions and methods of the invention include, but are not limited to, hydroxypropylcellulose, hydoxypropylmethylcellulose (HPMC), chitosan, polyacrylic acid, and polymethacrylic acid.

In one embodiment, the polymer is HPMC.

In one embodiment, the polymer is hydroxypropylcellulose,

In one embodiment, the polymer is polyacrylic acid. In one embodiment, the polyacrylic acid is a crosslinked polyacrylic acid such as Carbomer® (commercially available from Carbomer, Inc. of Westborough, Mass.).

In one embodiment, the polymer is polymethacrylic acid.

Typically, the polymer is present in an amount ranging from greater than 0 to 10 percent by weight of the pharmaceutical composition.

In one embodiment, the polymer is present in an amount ranging from about 0.1 to 10 percent by weight of the pharmaceutical composition.

In one embodiment, the polymer is present in an amount ranging from about 1 to 7.5 percent by weight of the pharmaceutical composition.

In one embodiment, the polymer is present in an amount ranging from about 1.5 to 5 percent by weight of the pharmaceutical composition.

In one embodiment, the polymer is present in an amount ranging from about 2 to 4 percent by weight of the pharmaceutical composition.

The components of the pharmaceutical composition (the polymer, the solvents, and the aptamer, as well as any other optional components) are preferably biocompatible and non-toxic and, over time, are simply absorbed and/or metabolized by the body.

In one embodiment, the pharmaceutical compositions of the invention are substantially free of polymers.

In one embodiment, any additional components added to the pharmaceutical compositions of the invention are designated as GRAS by the FDA for use or consumption by animals.

In another embodiment, any additional components added to the pharmaceutical compositions of the invention are designated as GRAS by the FDA for use or consumption by humans.

7.4.2 Representative Pharmaceutical Compositions

In one embodiment, the first organic solvent is propylene carbonate, the second organic solvent is glycerol formal, and the phospholipid is $$\begin{array}{c} R_3-O-CH_2 \\ | \\ R_2-O-CH \quad\quad O \\ | \quad\quad \| \\ CH_2-O-P-O-CH_2CH_2-N(CH_3)_3{}^+ \\ | \\ R_1 \end{array}$$

wherein $R_2$ and $R_3$ each are a stearoyl group or a palmitoyl group and the ratio of total stearoyl groups to palmitoyl groups is about 85:15 and $R_1$ is $O^-$ (Phospholipon® 90H, commercially available from Phospholipid GmbH of Cologne, Germany).

In one embodiment, the first organic solvent is propylene carbonate, the second organic solvent is glycerol formal, the phospholipid is Phospholipon® 90H, and the ratio of the propylene carbonate to the glycerol formal ranges from about 60:40 to 40:60.

In one embodiment, the first organic solvent is propylene carbonate, the second organic solvent is glycerol formal, the phospholipid is Phospholipon® 90H, and the ratio of the propylene carbonate to the glycerol formal is about 50:50.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the phospholipid is present in an amount of about 1 to 4 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, and the phospholipid is present in an amount of about 1 to 4 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the phospholipid is present in an amount of about 3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, and the phospholipid is present in an amount of about 3 percent by weight of the pharmaceutical composition.

In one embodiment, the first organic solvent is propylene carbonate, the second organic solvent is glycerol formal, the phospholipid is Phospholipon® 90H, and the aptamer is selected from the group consisting of ARC224, ARC245, ARC225, ARC259 (each identified in P. Burmeister et al., *Direct In Vitro Selection of a 2'-O-methyl Aptamer to VEGF*, Chemistry and Biology, vol. 12, 25-33, January 2005), and pegylated ARC259.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the aptamer is selected from the group consisting of ARC224, ARC245, ARC225, ARC259 (each identified in P. Burmeister et al., *Direct In Vitro Selection of a 2'-O-methyl Aptamer to VEGF*, Chemistry and Biology, vol. 12, 25-33, January 2005), and pegylated ARC259.

In one embodiment, the first organic solvent is propylene carbonate, the second organic solvent is glycerol formal, the phospholipid is Phospholipon® 90H, the ratio of the propylene carbonate to the glycerol formal is about 50:50, and the aptamer is selected from the group consisting of ARC224, ARC245, ARC225, ARC259 (each identified in P. Burmeister et al., *Direct In Vitro Selection of a 2'-O-methyl Aptamer to VEGF*, Chemistry and Biology, vol. 12, 25-33, January 2005), and pegylated ARC259.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the aptamer is selected from the group consisting of ARC224, ARC245, ARC225, ARC259 (each identified in P. Burmeister et al., *Direct In Vitro Selection of a 2'-O-methyl Aptamer to VEGF*, Chemistry and Biology, vol. 12, 25-33, January 2005) and pegylated ARC259.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the aptamer is selected from the group consisting of ARC224, ARC245, ARC225, ARC259 (each identified in P. Burmeister et al., *Direct In Vitro Selection of a 2'-O-methyl Aptamer to VEGF*, Chemistry and Biology, vol. 12, 25-33, January 2005), and pegylated ARC259.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the aptamer is selected from the group consisting of ARC224, ARC245, ARC225, ARC259 (each identified in P. Burmeister et al., *Direct In Vitro Selection of a 2'-O-methyl Aptamer to VEGF*, Chemistry and Biology, vol. 12, 25-33, January 2005), and pegylated ARC259.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the aptamer is selected from the group consisting of ARC224, ARC245, ARC225, ARC259 (each identified in P. Burmeister et al., *Direct In Vitro Selection of a 2'-O-methyl Aptamer to VEGF*, Chemistry and Biology, vol. 12, 25-33, January 2005) and pegylated ARC259.

In one embodiment, the first organic solvent is propylene carbonate, the second organic solvent is glycerol formal, the phospholipid is Phospholipon® 90H, and the aptamer is pegylated ARC259.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the aptamer is pegylated ARC259.

In one embodiment, the first organic solvent is propylene carbonate, the second organic solvent is glycerol formal, the phospholipid is Phospholipon® 90H, the ratio of the propylene carbonate to the glycerol formal is about 50:50, and the aptamer is pegylated ARC259.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the aptamer is pegylated ARC259.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the aptamer is pegylated ARC259.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the aptamer is pegylated ARC259.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the aptamer is pegylated ARC259.

In each pharmaceutical composition described above, the glycerol formal can be replaced with propylene glycol.

In one embodiment, the solvent is propylene glycol, glycerol formal, or a mixture thereof and the phospholipid is Phospholipon® 90H (commercially available from Phospholipid GmbH of Cologne, Germany). In one embodiment, the propylene glycol is substantially free of other organic solvents and the glycerol formal is substantially free of other organic solvents.

In one embodiment, the solvent is propylene glycol, glycerol formal, or a mixture thereof, the phospholipid is Phospholipon® 90H, and the phospholipid is present in an amount of about 1 to 4 percent by weight of the pharmaceutical composition. In one embodiment, the propylene glycol is substantially free of other organic solvents and the glycerol formal is substantially free of other organic solvents.

In one embodiment, the solvent is propylene glycol, glycerol formal, or a mixture thereof, the phospholipid is Phospholipon® 90H, and the phospholipid is present in an amount of about 1 to 2 percent by weight of the pharmaceutical composition. In one embodiment, the propylene glycol is substantially free of other organic solvents and the glycerol formal is substantially free of other organic solvents.

In one embodiment, the solvent is propylene glycol, glycerol formal, or a mixture thereof, the phospholipid is Phospholipon® 90H, and the aptamer is pegylated ARC259. In one embodiment, the propylene glycol is substantially free of other organic solvents and the glycerol formal is substantially free of other organic solvents.

In one embodiment, the solvent is propylene glycol, glycerol formal, or a mixture thereof, the phospholipid is Phospholipon® 90H, the phospholipid is present in an amount of about 1 to 4 percent by weight of the pharmaceutical composition, and the aptamer is pegylated ARC259. In one embodiment, the propylene glycol is substantially free of other organic solvents and the glycerol formal is substantially free of other organic solvents.

In one embodiment, the solvent is propylene glycol, glycerol formal, or a mixture thereof, the phospholipid is Phospholipon® 90H, the phospholipid is present in an amount of about 1 to 2 percent by weight of the pharmaceutical composition, and the aptamer is pegylated ARC259. In one embodiment, the propylene glycol is substantially free of other organic solvents and the glycerol formal is substantially free of other organic solvents.

In one embodiment, the solvent is propylene glycol, glycerol formal, or a mixture thereof, the phospholipid is Phospholipon® 90H, and the aptamer is selected from the group consisting of ARC224, ARC245, ARC225, ARC259 (each identified in P. Burmeister et al., *Direct In Vitro Selection of a 2'-O-methyl Aptamer to VEGF*, Chemistry and Biology, vol. 12, 25-33, January 2005) and pegylated ARC259. In one embodiment, the propylene glycol is substantially free of other organic solvents and the glycerol formal is substantially free of other organic solvents.

In one embodiment, the solvent is propylene glycol, glycerol formal, or a mixture thereof, the phospholipid is Phospholipon® 90H, the phospholipid is present in an amount of about 1 to 4 percent by weight of the pharmaceutical composition, and the aptamer is selected from the group consisting of ARC224, ARC245, ARC225, ARC259 (each identified in P. Burmeister et al., *Direct In Vitro Selection of a 2'-O-methyl Aptamer to VEGF*, Chemistry and Biology, vol. 12, 25-33, January 2005), and pegylated ARC259. In one embodiment, the propylene glycol is substantially free of other organic solvents and the glycerol formal is substantially free of other organic solvents.

In one embodiment, the solvent is propylene glycol, glycerol formal, or a mixture thereof, the phospholipid is Phospholipon® 90H, the phospholipid is present in an amount of about 1 to 2 percent by weight of the pharmaceutical composition, and the aptamer is selected from the group consisting of ARC224, ARC245, ARC225, ARC259 (each identified in P. Burmeister et al., *Direct In Vitro Selection of a 2'-O-methyl Aptamer to VEGF*, Chemistry and Biology, vol. 12, 25-33, January 2005), and pegylated ARC259. In one embodiment, the propylene glycol is substantially free of other organic solvents and the glycerol formal is substantially free of other organic solvents.

7.5 Methods of Treating a Condition in an Animal

The pharmaceutical compositions of the invention are useful in human medicine and veterinary medicine. Accordingly, the invention further relates to a method of treating or preventing a condition in an animal comprising administering to the animal an effective amount of the pharmaceutical composition of the invention.

In one embodiment, the invention relates to methods of treating a condition in an animal comprising administering to an animal in need thereof an effective amount of a pharmaceutical composition of the invention.

In one embodiment, the invention relates to methods of preventing a condition in an animal comprising administering to an animal in need thereof an effective amount of a pharmaceutical composition of the invention.

Methods of administration include, but are not limited to, intradermal, intramuscular, intraperitoneal, subcutaneous, intranasal, epidural, oral, sublingual, intracerebral, intravaginal, transdermal, rectal, or topical. The mode of administration is left to the discretion of the practitioner. In most instances, administration will result in the release of the aptamer into the bloodstream.

In one embodiment, the method of treating or preventing a condition in an animal comprises administering to the animal in need thereof an effective amount of an aptamer by parenterally administering the pharmaceutical composition of the invention. In one embodiment, the pharmaceutical compositions are administered by infusion or bolus injection. In one embodiment, the pharmaceutical composition is administered subcutaneously. In one embodiment, the pharmaceutical composition is administered subcutaneously and provides a drug depot in the animal that slowly releases the aptamer over time.

In one embodiment, the method of treating or preventing a condition in an animal comprises administering to the animal in need thereof a therapeutically effective amount of a pharmaceutically active agent by orally administering a pharmaceutical composition of the invention. To administer the pharmaceutical compositions orally, the pharmaceutical composition can, for example, be encapsulated in a capsule, such as a hard gelatin capsule or a soft gelatin capsule, and the capsule orally administered to the animal. Suitable capsules for use in the invention are Shionogi Qualicaps (commercially available from Shionogi & Co., Ltd of Osaka, Japan). Oral dosage forms can be designed to release the pharmaceutically active compound in the stomach immediately or almost immediately or to provide sustained release of the pharmaceutically active compound in the stomach. The oral dosage forms can also be designed to release the pharmaceutically active compound in the intestines immediately or almost immediately or to provide sustained release of the pharmaceutically active compound in the intestines. To delay the release of the pharmaceutically active compound until the dosage form reaches the intestines, the capsule is coated with an enteric coating. Typically, the enteric coating is a pH sensitive polymer such as Eudragit® L-100 (commercially available from DeGussa AG of Frankfurt, Germany). The rate of release of the pharmaceutically active compound is varied by varying the amount of phospholipid or sphingomyelin in the pharmaceutical composition and the presence of polymers in the pharmaceutical composition.

In one embodiment, the method of treating or preventing a condition in an animal comprises administering to the animal in need thereof a therapeutically effective amount of a pharmaceutically active agent by otically applying a pharmaceutical composition of the invention.

In one embodiment, the method of treating or preventing a condition in an animal comprises administering to the animal in need thereof a therapeutically effective amount of a pharmaceutically active agent by ophthalmically applying a pharmaceutical composition of the invention.

The pharmaceutical compositions can also be administered topically, by absorption through epithelial or mucocutaneous linings (e.g., oral, rectal, and intestinal mucosa, etc.). In one embodiment, the method of treating or preventing a condition in an animal comprises administering to the animal in need thereof a therapeutically effective amount of a pharmaceutically active agent by topically applying a pharmaceutical composition of the invention. The pharmaceutical compositions of the invention adhere well to the skin and, accordingly, are useful for topical application.

The pharmaceutical compositions of the invention are viscous compositions. Viscous compositions containing can have advantages over less viscous (thinner) liquid formulations for treating or preventing conditions in animals. For example, in topical applications, otic applications, and ophthalmic applications, especially veterinary uses, thinner liquid formulations are easily washed or swept away from a target area of delivery than formulations that are more viscous (thicker). For treating conditions, the advantages of thicker pharmaceutical compositions include maintaining the aptamer in the target area for longer periods of time.

The pharmaceutical compositions can be administered systemically or locally.

The pharmaceutical compositions can be administered together with another biologically active agent.

The effective amount administered to the animal depends on a variety of factors including, but not limited to the type of animal being treated, the condition being treated, the severity of the condition, and the specific aptamer being administered. One of ordinary skill in the art will readily know what is an effective amount of the pharmaceutical composition to treat a condition in an animal.

The pharmaceutical compositions of the invention can be used to treat any condition that is responsive to an aptamer.

In one embodiment, the aptamer is a anti-Vascular Endothelial Growth Factor (VEGF) aptamer. In one embodiment, the aptamer is a anti-Vascular Endothelial Growth Factor (VEGF) aptamer and the disorder is an ocular disorder. Representative ocular disorders include, but are not limited to, age-related macular degeneration, optic disc neovascularization, iris neovascularization, retinal neovascularization, choroidal neovascularization, corneal neovascularization, vitreal neovascularization, glaucoma, pannus, pterygium, macular edema, vascular retinopathy, retinal degeneration, uveitis, inflammatory diseases of the retina, or proliferative vitreoretinopathy. Virtually any method of delivering a medication to the eye may be used for the delivery of the pharmaceutical compositions of the invention. In one embodiment, the pharmaceutical composition is administered intravitreally, for example, via intravitreal injection. In one embodiment, the pharmaceutical composition is administered transclerally.

In one embodiment, the aptamer is an aptamer that inhibits angiogenesis.

In one embodiment, the aptamer is an aptamer that inhibits angiogenesis and the disease being treated is cancer. In one embodiment, the aptamer is an aptamer that inhibits angiogenesis and the disease being treated is a solid tumor.

In one embodiment, the pharmaceutical compositions according to the invention provide controlled- or sustained-release of the aptamer in an effective amount for at least about 4 to about 15 days. Some, pharmaceutical compositions, however, can provide controlled- or sustained-release of the aptamer in an effective amount effective amount for more than 15 days In another embodiment, the pharmaceutical compositions according to the invention provide controlled- or sustained-release of the aptamer in an effective amount effective amount for at least about 4 to about 10 days.

In another embodiment, the pharmaceutical compositions according to the invention provide controlled- or sustained-release of the aptamer in an effective amount effective amount for at least about 1 week.

In another embodiment, the pharmaceutical compositions according to the invention provide controlled- or sustained-release of the aptamer in an effective amount effective amount for at least about 1 to about 4 days.

In another embodiment, the pharmaceutical compositions according to the invention provide controlled- or sustained-release of the aptamer in an effective amount effective amount for at least about 1 to about 2 days.

The amount of the aptamer(s) that is (are) effective in treating or preventing a condition can be determined by standard clinical techniques. In addition, in vitro or in vivo assays can optionally be employed to help identify optimal dosage ranges. The precise dose to be employed will also depend on the route of administration, the seriousness of the condition, and the animal being treated and can be decided according to the judgment of a practitioner and/or each animal's circumstances. The effective dosage amounts described herein refer to total amounts of all aptamers administered; that is, if more than one aptamer is administered, the effective dosage amounts correspond to the total amount administered.

Typically, pharmaceutical composition is administered from about 1 time each day to about 1 time each week until the condition is abated. The pharmaceutical composition, however, can be administered less frequently or more frequently.

In one embodiment, the pharmaceutical composition is administered once each day until the condition is abated.

In one embodiment, the pharmaceutical composition is administered twice each day until the condition is abated.

In one embodiment, the pharmaceutical composition is administered once each week until the condition is abated.

In one embodiment, the pharmaceutical composition is administered twice each week until the condition is abated.

In one embodiment, the pharmaceutical composition is administered about every 12 hours until the condition is abated.

In one embodiment, the pharmaceutical composition is administered about every 2 weeks until the condition is abated.

In one embodiment, the pharmaceutical composition is administered a single time.

In one embodiment, the pharmaceutical composition is administered daily for 1 week.

In one embodiment, the pharmaceutical composition is administered about every 7 days for 4 weeks.

In one embodiment, the pharmaceutical composition is administered about every 7 days for 3 weeks.

In one embodiment, the pharmaceutical composition is administered about every 7 days for 2 weeks.

In one embodiment, the pharmaceutical composition is administered twice about 24 hours apart.

In one embodiment, the pharmaceutical composition is administered twice about 48 hours apart.

In one embodiment, the pharmaceutical composition is administered about every 24 hours for about 4 weeks.

In one embodiment, the pharmaceutical composition is administered about every 12 hours for about 4 weeks.

In one embodiment, the pharmaceutical composition is administered about every 24 hours for about 2 weeks.

In one embodiment, the pharmaceutical composition is administered about every 12 hours for about 2 weeks.

In one embodiment, the pharmaceutical composition is administered about every 24 hours for about 1 week.

In one embodiment, the pharmaceutical composition is administered about every 12 hours for about 1 week.

In another embodiment, an effective dosage amount is administered daily until the condition is abated. The total dose may optionally be divided into daily doses and/or into about 2 to 4 individual doses.

Without being bound by theory, it is believed that the pharmaceutical compositions of the invention wherein the pharmaceutical composition is in the form of a gel containing the aptamer(s) allows for higher loading than can be attained with liposomal formulations (where the maximum loading is believed to be only about 1 percent by weight of the liposome-containing composition). Indeed, pharmaceutical composition containing homogenously distributed aptamer in as much as about 12 percent by weight of the pharmaceutical compositions, and even more, are routinely possible using the compositions of the invention. The pharmaceutical compositions of the invention are preferably substantially free of liposomes. In one embodiment, the pharmaceutical compositions of the invention are free of liposomes.

In one embodiment, the animal is a non-human animal.
In another embodiment, the animal is a human.
In one embodiment, the animal is a mammal.
In one embodiment, the animal is a canine, a feline, an equine, a bovine, an ovine, a porcine, or an avian.
In one embodiment, the animal is a cat.
In one embodiment, the animal is a dog.
In one embodiment, the animal is a cow.
In one embodiment, the animal is a pig.
In one embodiment, the animal is a sheep.
In one embodiment, the animal is a horse.

7.6 Preparing the Pharmaceutical Compositions

The pharmaceutical compositions of the invention comprising (i) a phospholipid or sphinhomelyelin; (ii) a first organic solvent; (iii) a second organic solvent; and (iv) an aptamer, can be prepared, for example, by simply adding the aptamer(s) to a mixture of the first organic solvent and the second organic solvent ("solvent mixture") (typically about 90% of the amount of the solvent mixture desired in the final pharmaceutical composition) and agitating or stirring the resulting mixture until the aptamer(s) dissolve(s). One or more optional additive(s) can simultaneously and/or sequentially be added and the mixture agitated or stirred until the optional additive(s) dissolve(s). The phospholipid is then added to the mixture, with agitation or stirring, and optionally with heat to provide a phospholipid mixture. Typically the mixture is heated at a temperature of less than 100° C., preferably less than 70° C., more preferably less than about 50° C., and most preferably about 40° C. before the phospholipid is added. Additional solvent mixture is then added to provide the desired concentration of the aptamer(s) in the pharmaceutical composition and the phospholipid mixture is allowed to cool to room temperature to provide the pharmaceutical composition.

Similarly the pharmaceutical compositions of the invention comprising (i) a phospholipid or sphingomyelin, a solvent of selected from the group consisting of propylene glycol substantially free of the other organic solvents and glycerol formal substantially free of other organic solvents, and (iii) an aptamer can be prepared, for example, by simply adding the aptamer(s) to the propylene glycol or glycerol formal (typically about 90% of the amount of the solvent desired in the final pharmaceutical composition) and agitating or stirring the resulting mixture, optionally with heat, until aptamer(s) dissolve(s). One or more optional additive(s) can simultaneously and/or sequentially be added and the mixture agitated or stirred until the optional additive(s) dissolve(s). The phospholipid is then added to the mixture, with agitation or stirring, and optionally with heat to provide a phospholipid mixture. Typically the mixture is heated at a temperature of less than 100° C., preferably less than 70° C., more preferably less than about 50° C., and most preferably about 40° C. before the phospholipid is added. Additional propylene glycol or glycerol formal is then added to provide the desired concentration of the aptamer(s) in the pharmaceutical composition and the phospholipid mixture is allowed to cool to room temperature to provide the pharmaceutical composition.

One skilled in the art, however, will readily recognize that modifications to the above-described methods for preparing the pharmaceutical compositions of the invention are possible, for example the order of adding the components to the solvent(s) can be changed. For example, pharmaceutical compositions comprising a protonated aptamer and ester or amide of lysine can be prepared by simply adding the protonated aptamer to the first organic solvent and second organic solvent (or propylene glycol substantially free of other organic solvents and glycerol formal substantially free of other organic solvents) and then simply adding the ester or amide of lysine, preferably, with stirring. To the resulting solution is then added the phospholipid, preferably with stirring and heating.

7.7 Kits

The invention encompasses kits that can simplify the administration of an aptamer to an animal. A typical kit of the invention comprises a unit dosage form of a pharmaceutical composition according to the invention. In one embodiment, the unit dosage form is a container (such as a vial, a pouch, a tube, a syringe, or the like), which can advantageously be sterile, containing a pharmaceutical composition of the invention. The kit can further comprise a label or printed instructions instructing the use of the aptamer to treat or prevent a condition. In another embodiment, the kit comprises a unit dosage form of a pharmaceutical composition of the invention and a dropper, syringe, or other applicator for administering the pharmaceutical composition. Typically, the components of the kit, for example, the unit dosage form and instructions, are contained within a suitable packaging material.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

8. EXAMPLES

Example 8.1

Preparation of Amino Acid Esters

Tryptophane butanoate: 1 g of tryptophane butanoate hydrochloride salt (commercially available from Sigma-Aldrich, St. Louis, Mo.) was suspended in 25 mL of dichloromethane and 600 μl of triethylamine was added to the suspension with stirring. Stirring was continued for 15 min and the resulting solution was transferred to a separatory funnel. The organic solution was washed twice with 25 mL of water followed by 25 mL of saturated aqueous sodium bicarbonate. The organic layer was then dried over anhydrous sodium sulfate and concentrated under reduced pressure to provide tryptophane butanoate. The structure was confirmed using mass spectroscopy.

Tryptophane octanoate: 4 g of tryptophane butanoate hydrochloride salt (commercially available from Sigma-Aldrich, St. Louis, Mo. (www.sima-aldrich.com)) was suspended in 100 mL of dichloromethane and 3 ml of triethylamine was added to the suspension with stirring. Stirring was continued for 15 min and the resulting solution was transferred to a separatory funnel. The organic solution was washed twice with 25 mL of water followed by 25 mL of saturated aqueous sodium bicarbonate. The organic layer was then dried over anhydrous sodium sulfate and concentrated under reduced pressure to provide tryptophane octanoate. The structure was confirmed using mass spectroscopy.

Tyrosine butanoate: 18.19 g of tyrosine was suspended in a solution of 9.8 g of concentrated sulfuric acid, 40 mL water, 40 mL of butanol, and 200 mL of toluene in a 500 mL round bottom flask equipped with a condenser and a Dean-Stark apparatus. The resulting solution was heated at reflux temperature until no more water could be distilled. The resulting solution was cooled in an ice bath, which caused the solution to separate into two phases. The upper phase was discarded and the lower phase, an oily syrup, was retained. The syrup was mixed with sufficient 5% aqueous sodium bicarbonate solution to neutralize acidic impurities to provide a solid that was collected by filtration and washed with cold water. The resulting solid was re-crystallized in ethyl acetate.

Isoleucine butyrate: 26.23 g of isoleucine was dissolved in a solution of 20 g of concentrated sulfuric acid, 20 mL water, 40 mL of butanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was removed under reduced pressure and the resulting liquid distilled under vacuum to provide isoleucine butyrate as a colorless liquid.

Phenylalanine butyrate: 16.52 g of isoleucine was dissolved in a solution of 10 g of concentrated sulfuric acid, 20 mL water, 20 mL of butanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was removed under reduced pressure and the resulting liquid distilled under vacuum to provide phenylalanine butyrate.

Phenylalanine octanoate: 16.52 g of phenylalanine was dissolved in a solution of 10 g of concentrated sulfuric acid, 20 mL water, 20 mL of octanol, and 120 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was then removed under reduced pressure to provide phenylalanine octanoate as a white solid that was purified using a silica gel column eluted with a 1:9 methanol:dichloromethane mixture.

Phenylalanine dodecanoate: 16.52 g of phenylalanine was dissolved in a solution of 10 g of concentrated sulfuric acid, 20 mL water, 20 mL of dodecanol, and 120 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was then removed under reduced pressure to provide phenylalanine dodecanoate as a solid that was purified using a silica gel column eluted with a 1:9 methanol:dichloromethane mixture.

Tyrosine octanoate: 9.06 g of tyrosine was dissolved in a solution of 10 g of concentrated sulfuric acid, 20 mL water, 10 mL of octanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities to provide an emulsion. About 150 mL of ethyl acetate was added to the emulsion to provide two phases. The aqueous phase was discarded and the organic phase washed with saturated Brine and dried over anhydrous sodium sulfate. The solvent was the removed under reduced pressure to provide tyrosine octanoate as a white solid that was purified using a silica gel column eluted with a 1:9 methanol:dichloromethane mixture.

Isoleucine octanoate: 13.1 g of isoleucine was dissolved in a solution of 10 g of concentrated sulfuric acid, 20 mL water, 20 mL of octanol, and 200 mL of toluene in a 500 mL round bottom flask equipped with a condenser and a Dean-Stark apparatus placed in an oil bath. The resulting solution was heated at reflux temperature until no more water could be distilled. The resulting solution was then cooled to room temperature, diluted with 120 mL of ethyl acetate and the organic layer washed with saturated aqueous sodium bicarbonate to neutralize acidic impurities, washed with saturated brine, and dried over anhydrous sodium sulfate. The solvent was removed under reduced pressure and the resulting liquid distilled to provide isoleucine octanoate as a colorless liquid.

Proline butanoate: 34.5 g of proline was suspended in a solution of 35 g of concentrated sulfuric acid, 40 mL water, 120 mL of butanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature, washed with saturated aqueous sodium bicarbonate to neutralize acidic impurities, washed with saturated brine, and dried over anhydrous sodium sulfate. The solvent was removed under reduced pressure and the resulting liquid distilled to provide proline butanoate as a colorless liquid.

Lysine hexadecanoate: BOC protected lysine (6.25 g, 0.018 mole) was dissolved in about 40 mL of tetrahydrofuran under a nitrogen atmosphere. The solution was cooled to about 0° C. using an ice-water bath and carbonyl diimidazole (2.93 g, 0.018 mole) was added to the cooled solution. The reaction mixture was then allowed to stir for about 5 min. at about 5° C. and then for about 30 min. at room temperature. To the resulting solution was then added by dropwise addition a solution of hexadecanol (4.38 g, 0.018 mole) in about 10 mL of tetrahydrofuran. The resulting solution was then warmed to about 45° C. and allowed to stir for about 12 h. After stirring, the solvent was evaporated under reduced pressure; the resulting residue dissolved in ethyl acetate; the ethyl acetate washed with 0.1 N hydrochloric acid (3 times), saturated aqueous sodium hydrogen carbonate (3 times), and brine (3 times); and the organic phase dried ($Na_2SO_4$). The ethyl acetate was then removed under reduced pressure to provide crude BOC protected lysine hexadecanoate that was purified using silica gel column chromatography eluted with 0 to 20 percent ethyl acetate in hexane. The solvent was then evaporated under reduced pressure to provide purified BOC protected lysine hexadecanoate. Trifluoroacetic acid (20 mL) was added to the purified BOC protected lysine hexadecanoate and the resulting reaction mixture stirred for about 5 h. Excess trifluoroacetic acid was removed under reduced pressure. The resulting residue was then dissolved in methanol and passed through a Dowex 550A(OH) resin (50 g) (commercially available from Dow Chemical Company of Midland Mich.) and the solvent removed under reduced pressure to provide lysine hexadecanoate that was dried under vacuum to provide dried lysine hexadecanoate (3.6 g).

Example 8.2

Phospholipid Composition Containing an Aptamer and an Amino Acid Ester

A: A pharmaceutical composition was prepared by dissolving 100 mg of pegylated ARC259 in 1.5 mL of glycerol formal. To the resulting mixture was then added 10 μL of isoleucine butyrate and the resulting solution mixed on a vortex mixer with intermittent sonication to provide a clear solution. To the resulting solution was added 40 mg of Phospholipon® 90H (commercially available from Phospholipid GmbH of Cologne, Germany or American Lecithin Company of Oxford, Conn.) and the resulting mixture heated to about 40° C. for 3 hours. The solution was then allowed to cool to room temperature to provide a gel.

The pharmaceutical composition, when heated to 40° C., advantageously provides a free flowing liquid that can be sterilized by filtration. The free flowing liquid can also be pre-loaded into syringes and, although the pharmaceutical composition forms a gel when it cools to room temperature, the gel can be easily dispensed from the syringe.

B: A pharmaceutical composition was prepared by dissolving 100 mg of pegylated ARC259 in 1 mL of propylene glycol. To the resulting mixture was then added 500 μL of glycerol formal and 10 μL of isoleucine butyrate and the resulting solution mixed on a vortex mixer with intermittent sonication to provide a clear solution. To the resulting solution was added 40 mg of Phospholipon® 90H (commercially available from Phospholipid GmbH of Cologne, Germany or American Lecithin Company of Oxford, Conn.) and the resulting mixture heated to about 40° C. for 2 hours. The solution was then allowed to cool to room temperature to provide a gel.

The pharmaceutical composition, when heated to 40° C., advantageously provides a free flowing liquid that can be sterilized by filtration. The free flowing liquid can also be pre-loaded into syringes and, although the pharmaceutical composition forms a gel when it cools to room temperature, the gel can be easily dispensed from the syringe.

Example 8.3

HPLC Analysis of the Pharmaceutical Compositions of the Invention and Method for Measuring Rate of Release of the Aptamer from the Pharmaceutical Compositions of the Invention The amount of aptamer released from the pharmaceutical composition of either Example 8.2 A or B as a function of time can be measured by injecting about 50 μL (50 μg) of the pharmaceutical composition into about 4 mL of deionized water in a centrifuge tube to form the precipitate. The time that the pharmaceutical composition is injected into the water is recorded as T=0. After a specified amount of time, T, the sample, optionally cooled to about −9° C., is spun on a centrifuge at about 13,000 rpm for about 20 min. to provide a pellet and a supernatant liquid that can be easily separated by decanting the supernatant. The resulting supernatant is then analyzed by a suitable HPLC method to determine the amount of aptamer present in the aqueous solution. The amount of aptamer in the pellet can also be determined by dissolving the pellet in about 3 mL of methanol and analyzing the methanol solution by a suitable HPLC method to determine the amount of aptamer in the precipitate. The amount of aptamer in the aqueous solution and the amount of aptamer in the precipitate can be determined by comparing the peak area for the HPLC peak corresponding to the aptamer against a standard curve of aptamer peak area against concentration of aptamer. Suitable HPLC methods can be readily determined by one of ordinary skill in the art. For example for the aptamer used in the above experiments (i.e., pegylated ARC259) the following HPLC method can be used:

| Column: | Jupiter 5μ C4 300 A, 30 × 4.6 mm (Part # 00A-4167-EO). |
|---|---|
| Flow rate: | 2.0 mL/min. |
| Injection volume: | 20 μL |
| Detector setting: | 258 nm |
| Run Time: | 10 min. |

-continued

| Pump A: | Option 1 (Acidic mobile phase): 25 mM Ammonium Acetate-Trifluoroacetic Acid (TFA), pH 4.76 or |
| Pump A: | Option 2 (Basic mobile phase): 50 mM Triethanolamine-HCl, pH 7.8 |
| Pump B: | Methanol |
| Initial Conditions: | 0% pump B    100% pump A |

The HPLC column is eluted using the following gradient elution profile:

| Time (min) | Module | Function | Value | Duration (min) |
|---|---|---|---|---|
| 0.00 | pump | % B | 90.00 | 3.00 |
| 6.00 | pump | % B | 0.00 | 0.50 |
| 6.00 | pump | Flow Rate | 4.00 | 0.00 |
| 10.00 | Detector | stop acquiring data | | |

Under these conditions the aptamer has a retention time of about 3 min.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated herein by reference.

What is claimed is:

1. A pharmaceutical composition comprising:
a phospholipid or sphingomyelin;
at least one organic solvent; and
an aptamer or a pharmaceutically acceptable salt thereof, wherein the phospholipid or sphingomyelin and at least one organic solvent are present in amounts sufficient to form a gel.

2. The pharmaceutical composition of claim 1, wherein the at least one organic solvent is a combination of a polar aprotic organic solvent and a polar protic organic solvent.

3. The pharmaceutical composition of claim 2, wherein the ratio of the protic organic solvent to the aprotic organic solvent ranges from about 90:10 to 10:90.

4. The pharmaceutical composition of claim 2, wherein the protic organic solvent is glycerol formal and the aprotic organic solvent propylene carbonate.

5. The pharmaceutical composition of claim 1, wherein the phospholipid has the general structure:

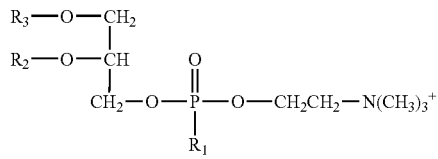

wherein $R_2$ and $R_3$ are each independently stearoyl groups or palmitoyl groups wherein the ratio of stearoyl groups to palmitoyl groups is about 85:15 and $R_1$ is $O^-$.

6. The pharmaceutical composition of claim 1, wherein the pharmaceutical composition has a viscosity ranging from about 1,000 cP to 75,000 cP at 25° C.

7. The pharmaceutical composition of claim 1, wherein the phospholipid is present in an amount ranging from about 0.1 percent to 10 percent by weight of the pharmaceutical composition.

8. The pharmaceutical composition of claim 7, wherein the phospholipid is present in an amount ranging from about 1 percent to 4 percent by weight of the pharmaceutical composition.

9. The pharmaceutical composition of claim 1, further comprising a polymer.

10. The pharmaceutical composition of claim 9, wherein the polymer is present in an amount ranging from about 0.1 to 10 percent by weight of the pharmaceutical composition.

11. The pharmaceutical composition of claim 9, wherein the polymer is hydroxypropylcellulose or hydroxypropylmethylcellulose.

12. The pharmaceutical composition of claim 4, wherein the phospholipid has the general structure:

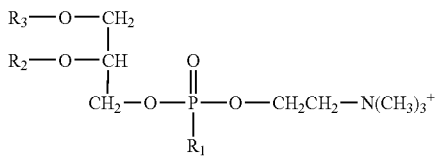

wherein $R_2$ and $R_3$ are each independently stearoyl groups or palmitoyl groups wherein the ratio of stearoyl groups to palmitoyl groups is about 85:15 and $R_1$ is $O^-$.

13. The pharmaceutical composition of claim 12, wherein the pharmaceutical composition has a viscosity ranging from about 1,000 cP to 75,000 cP at 25° C.

14. The pharmaceutical composition of claim 1, wherein the aptamer or a pharmaceutically acceptable salt thereof is present in an amount of greater than about 1 percent by weight of the pharmaceutical composition.

15. The pharmaceutical composition of claim 1, wherein the aptamer or a pharmaceutically acceptable salt thereof is present in an amount ranging from about 1 to 15 percent by weight of the pharmaceutical composition.

16. The pharmaceutical composition of claim 1, wherein the aptamer or a pharmaceutically acceptable salt thereof is present as an aptamer composition comprising a salt formed between (i) a protonated aptamer and (ii) a pharmaceutically acceptable organic base.

17. The pharmaceutical composition of claim 16, wherein the pharmaceutically acceptable organic base is selected from the group consisting of cyclohexylamine; cyclopentylamine; cyclohexylamine; dicyclohexylamine; tributyl amine; N-methylamine; N-ethylamine; diethylamine; dimethylamine; triethylamine; mono-, bis-, or tris-(2-hydroxyethyl)amine; 2-hydroxy-tert-butylamine; tris-(hydroxymethyl)methylamine; N,N,-dimethyl-N-(2-hydroxyethyl)amine; N,N,-dialkyl-N-tris-(2-hydroxyethyl)amines); pyridine; benzylamine; phenethylamine; N-methyl-D-glucamine; N,N'-dibenzylethylenediamine; chloroprocaine; choline; procaine, amino acids, and amino acid esters and amides.

18. The pharmaceutical composition of claim 1, wherein the aptamer or a pharmaceutically acceptable salt thereof is present as an aptamer composition comprising a salt formed between (i) a protonated aptamer and (ii) an amino acid ester or amide, wherein the amino acid ester has the structure:

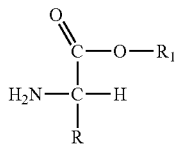

wherein

R is the amino acid side chain; and $R_1$ is a $C_1$ to $C_{22}$ hydrocarbon group; or and the amino acid amide has the structure:

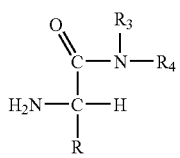

wherein

R is the amino acid side chain;

$R_3$ is a $C_1$ to $C_{22}$ hydrocarbon group; and $R_4$ is hydrogen or a $C_1$ to $C_{22}$ hydrocarbon group.

19. The pharmaceutical composition of claim 18, wherein the amino acid ester or amide is an ester or amide of lysine.

20. The pharmaceutical composition of claim 19, further comprising a carboxylic acid.

21. The pharmaceutical composition of claim 20, wherein the carboxylic acid is a fatty acid.

22. The pharmaceutical composition of claim 1, wherein the aptamer or a pharmaceutically acceptable salt thereof is present as an aptamer composition comprising a salt formed between (i) a protonated aptamer and (ii) a polylysine.

23. The pharmaceutical composition of claim 1, wherein the aptamer or a pharmaceutically acceptable salt thereof is present as an aptamer composition comprising (i) the aptamer and (ii) a divalent metal cation.

24. The pharmaceutical composition of claim 23, wherein the aptamer composition further comprises a carboxylate.

25. The pharmaceutical composition of claim 1, wherein the at least one organic solvent is selected from the group consisting of propylene glycol substantially free of other organic solvents, glycerol formal substantially free of other organic solvents, and mixtures thereof.

26. The pharmaceutical composition of claim 25, wherein the solvent is propylene glycol substantially free of other organic solvents.

27. The pharmaceutical composition of claim 25, wherein the organic solvent is glycerol formal substantially free of other organic solvents.

28. The pharmaceutical composition of claim 25, wherein the organic solvent is a mixture of propylene glycol substantially free of other organic solvents and glycerol formal substantially free of other organic solvents.

29. The pharmaceutical composition of claim 25, wherein the phospholipid has the general structure:

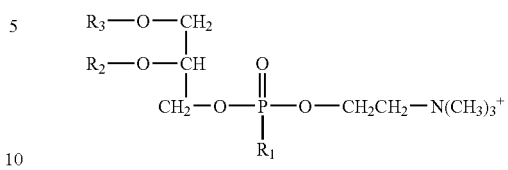

wherein $R_2$ and $R_3$ are each independently stearoyl groups or palmitoyl groups wherein the ratio of stearoyl groups to palmitoyl groups is about 85:15 and $R_1$ is $O^-$.

30. The pharmaceutical composition of claim 25, wherein the pharmaceutical composition has a viscosity ranging from about 1,000 cP to 75,000 cP at 25° C.

31. The pharmaceutical composition of claim 25, wherein the phospholipid or sphingomyelin is present in an amount ranging from about 0.1 percent to 10 percent by weight of the pharmaceutical composition.

32. The pharmaceutical composition of claim 31, wherein the phospholipid or sphingomyelin is present in an amount ranging from about 1 percent to 4 percent by weight of the pharmaceutical composition.

33. The pharmaceutical composition of claim 25, further comprising a polymer.

34. The pharmaceutical composition of claim 33, wherein the polymer is present in an amount ranging from about 0.1 to 10 percent by weight of the pharmaceutical composition.

35. The pharmaceutical composition of claim 33, wherein the polymer is hydroxypropylcellulose or hydroxypropylmethylcellulose.

36. The pharmaceutical composition of claim 25, wherein the aptamer or a pharmaceutically acceptable salt thereof is present in an amount of greater than about 1 percent by weight of the pharmaceutical composition.

37. The pharmaceutical composition of claim 25, wherein the aptamer or a pharmaceutically acceptable salt thereof is present in an amount ranging from about 1 to 15 percent by weight of the pharmaceutical composition.

38. The pharmaceutical composition of claim 25, wherein the aptamer or a pharmaceutically acceptable salt thereof is present as an aptamer composition comprising (i) a salt formed between a protonated aptamer and (ii) a pharmaceutically acceptable organic base.

39. The pharmaceutical composition of claim 38, wherein the pharmaceutically acceptable organic base is selected from the group consisting of cyclohexylamine; cyclopentylamine; cyclohexylamine; dicyclohexylamine; tributyl amine; N-methylamine; N-ethylamine; diethylamine; dimethylamine; triethylamine; mono-, bis-, or tris-(2-hydroxyethyl)amine; 2-hydroxy-tert-butylamine, tris-(hydroxymethyl)methylamine; N,N,-dimethyl-N-(2-hydroxyethyl)amine; N,N,-dialkyl-N-tris-(2-hydroxyethyl)amines); pyridine; benzylamine; phenethylamine; N-methyl-D-glucamine; N,N'-dibenzylethylenediamine; chloroprocaine; choline; procaine, amino acids, and amino acid esters or amides.

40. The pharmaceutical composition of claim 25, wherein the aptamer or a pharmaceutically acceptable salt thereof is present as an aptamer composition comprising a salt formed between (i) a protonated aptamer and (ii) an amino acid ester or amide, wherein the amino acid ester has the structure:

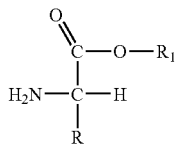

wherein

R is the amino acid side chain; and $R_1$ is a $C_1$ to $C_{22}$ hydrocarbon group; or and the amino acid amide has the structure:

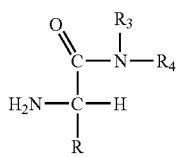

wherein

R is the amino acid side chain;

$R_3$ is a $C_1$ to $C_{22}$ hydrocarbon group; and $R_4$ is hydrogen or a $C_1$ to $C_{22}$ hydrocarbon group.

41. The pharmaceutical composition of claim 40, wherein the amino acid ester or amide is an ester or amide of lysine.

42. The pharmaceutical composition of claim 41, further comprising a carboxylic acid.

43. The pharmaceutical composition of claim 42, wherein the carboxylic acid is a fatty acid.

44. The pharmaceutical composition of claim 25, wherein the aptamer or a pharmaceutically acceptable salt thereof is present as an aptamer composition comprising a salt formed between (i) a protonated aptamer and (ii) a polylysine.

45. The pharmaceutical composition of claim 25, wherein the aptamer or a pharmaceutically acceptable salt thereof is present as an aptamer composition comprising (i) the aptamer and (ii) a divalent metal cation.

46. The pharmaceutical composition of claim 45, wherein the aptamer composition further comprises a carboxylate.

47. The pharmaceutical composition of claim 46, wherein the carboxylate is a carboxylate of a fatty acid.

48. The pharmaceutical composition of claim 1 wherein the at least one organic solvent comprises: (a) a first solvent is selected from the group consisting of propylene glycol substantially free of other organic solvents, glycerol formal substantially free of other organic solvents, and mixtures thereof and (b) N-methyl pyrollidone.

49. The pharmaceutical composition of claim 48, wherein the first solvent is propylene glycol substantially free of other organic solvents.

50. The pharmaceutical composition of claim 48, wherein the first organic solvent is glycerol formal substantially free of other organic solvents.

51. The pharmaceutical composition of claim 48, wherein the first solvent is a mixture of propylene glycol substantially free of other organic solvents and glycerol formal substantially free of other organic solvents.

52. The pharmaceutical composition of claim 48, wherein the phospholipid has the general structure:

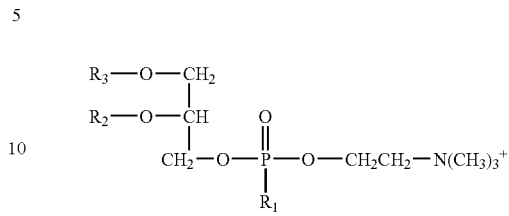

wherein $R_2$ and $R_3$ are each independently stearoyl groups or palmitoyl groups wherein the ratio of stearoyl groups to palmitoyl groups is about 85:15 and $R_1$ is $O^-$.

53. The pharmaceutical composition of claim 48, wherein the pharmaceutical composition has a viscosity ranging from about 1,000 cP to 75,000 cP at 25° C.

54. The pharmaceutical composition of claim 48, wherein the phospholipid or sphingomyelin is present in an amount ranging from about 0.1 percent to 10 percent by weight of the pharmaceutical composition.

55. The pharmaceutical composition of claim 54, wherein the phospholipid or sphingomyelin is present in an amount ranging from about 1 percent to 4 percent by weight of the pharmaceutical composition.

56. The pharmaceutical composition of claim 48, further comprising a polymer.

57. The pharmaceutical composition of claim 56, wherein the polymer is present in an amount ranging from about 0.1 to 10 percent by weight of the pharmaceutical composition.

58. The pharmaceutical composition of claim 56, wherein the polymer is hydroxypropylcellulose or hydroxypropylmethylcellulose.

59. The pharmaceutical composition of claim 48, wherein the aptamer or a pharmaceutically acceptable salt thereof is present in an amount of greater than about 1 percent by weight of the pharmaceutical composition.

60. The pharmaceutical composition of claim 48, wherein the aptamer or a pharmaceutically acceptable salt thereof is present in an amount ranging from about 1 to 15 percent by weight of the pharmaceutical composition.

61. The pharmaceutical composition of claim 48, wherein the aptamer or a pharmaceutically acceptable salt thereof is present as an aptamer composition comprising (i) a salt formed between a protonated aptamer and (ii) a pharmaceutically acceptable organic base.

62. The pharmaceutical composition of claim 61 wherein the pharmaceutically acceptable organic base is selected from the group consisting of cyclohexylamine; cyclopentylamine; cyclohexylamine; dicyclohexylamine; tributyl amine; N-methylamine; N-ethylamine; diethylamine; dimethylamine; triethylamine; mono-, bis-, or tris-(2-hydroxyethyl)amine; 2-hydroxy-tert-butylamine; tris-(hydroxymethyl)methylamine; N,N,-dimethyl-N-(2-hydroxyethyl)amine; N,N,-dialkyl-N-tris-(2-hydroxyethyl)amines); pyridine; benzylamine; phenethylamine; N-methyl-D-glucamine; N,N'-dibenzylethylenediamine; chloroprocaine; choline; procaine, amino acids, and amino acid esters or amides.

63. The pharmaceutical composition of claim 48, wherein the aptamer or a pharmaceutically acceptable salt thereof is present as an aptamer composition comprising a salt formed between (i) a protonated aptamer and (ii) an amino acid ester or amide, wherein the amino acid ester has the structure:

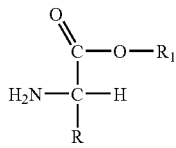

wherein
R is the amino acid side chain; and
$R_1$ is a $C_1$ to $C_{22}$ hydrocarbon group; or
and the amino acid amide has the structure:

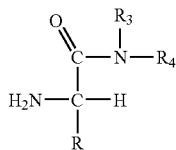

wherein
R is the amino acid side chain;
$R_3$ is a $C_1$ to $C_{22}$ hydrocarbon group; and
$R_4$ is hydrogen or a $C_1$ to $C_{22}$ hydrocarbon group.

64. The pharmaceutical composition of claim 63, wherein the amino acid ester or amide is an ester or amide of lysine.

65. The pharmaceutical composition of claim 64, further comprising a carboxylic acid.

66. The pharmaceutical composition of claim 65, wherein the carboxylic acid is a fatty acid.

67. The pharmaceutical composition of claim 48, wherein the aptamer or a pharmaceutically acceptable salt thereof is present as an aptamer composition comprising a salt formed between (i) a protonated aptamer and (ii) a polylysine.

68. The pharmaceutical composition of claim 48, wherein the aptamer or a pharmaceutically acceptable salt thereof is present as an aptamer composition comprising (i) the aptamer and (ii) a divalent metal cation.

69. The pharmaceutical composition of claim 68, wherein the aptamer composition further comprises a carboxylate.

70. The pharmaceutical composition of claim 68, wherein the carboxylate is a carboxylate of a fatty acid.

* * * * *